US012799198B2

(12) United States Patent
Shimasaki et al.

(10) Patent No.: US 12,799,198 B2
(45) Date of Patent: Nov. 17, 2026

(54) FUNCTIONAL BINDERS SYNTHESIZED AND SECRETED BY IMMUNE CELLS

(71) Applicant: National University of Singapore, Singapore (SG)

(72) Inventors: Noriko Shimasaki, Singapore (SG); Dario Campana, Singapore (SG)

(73) Assignee: National University of Singapore, Singapore (SG)

( * ) Notice: Subject to any disclaimer, the term of this patent is extended or adjusted under 35 U.S.C. 154(b) by 1347 days.

(21) Appl. No.: 17/597,582

(22) PCT Filed: Jul. 15, 2020

(86) PCT No.: PCT/IB2020/056659
§ 371 (c)(1),
(2) Date: Jan. 12, 2022

(87) PCT Pub. No.: WO2021/009694
PCT Pub. Date: Jan. 21, 2021

(65) Prior Publication Data

US 2022/0281971 A1 Sep. 8, 2022

Related U.S. Application Data

(60) Provisional application No. 62/875,455, filed on Jul. 17, 2019.

(51) Int. Cl.

| | |
|---|---|
| ***C07K 16/28*** | (2006.01) |
| ***A61K 40/11*** | (2025.01) |
| ***A61K 40/15*** | (2025.01) |
| ***A61K 40/42*** | (2025.01) |
| ***C07K 14/54*** | (2006.01) |
| ***C07K 14/705*** | (2006.01) |
| ***C12N 5/0783*** | (2010.01) |

(52) U.S. Cl.
CPC .......... *C07K 16/2803* (2013.01); *A61K 40/11* (2025.01); *A61K 40/15* (2025.01); *A61K 40/4211* (2025.01); *A61K 40/4221* (2025.01); *C07K 14/5443* (2013.01); *C07K 14/70517* (2013.01); *C07K 14/70575* (2013.01); *C07K 16/2887* (2013.01); *C12N 5/0636* (2013.01); *C12N 5/0646* (2013.01); *A61K 2239/31* (2023.05); *A61K 2239/38* (2023.05); *A61K 2239/48* (2023.05); *C07K 2317/24* (2013.01); *C07K 2317/52* (2013.01); *C07K 2317/622* (2013.01); *C07K 2317/732* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 5,595,756 | A | 1/1997 | Bally et al. |
| 7,435,596 | B2 | 10/2008 | Campana et al. |
| 7,932,055 | B2 | 4/2011 | Spee et al. |
| 8,026,097 | B2 | 9/2011 | Campana et al. |
| 8,399,645 | B2 | 3/2013 | Campana et al. |
| 9,511,092 | B2 | 12/2016 | Campana et al. |
| 9,605,049 | B2 | 3/2017 | Campana et al. |
| 10,428,305 | B2 | 10/2019 | Campana et al. |
| 10,538,739 | B2 | 1/2020 | Campana et al. |
| 10,736,920 | B2 | 8/2020 | Yu et al. |
| 10,774,309 | B2 | 9/2020 | Campana et al. |
| 10,774,311 | B2 | 9/2020 | Campana et al. |
| 10,801,012 | B2 | 10/2020 | Campana et al. |
| 10,829,737 | B2 | 11/2020 | Campana et al. |
| 10,836,999 | B2 | 11/2020 | Campana et al. |
| 11,141,436 | B2 | 10/2021 | Trager et al. |
| 11,154,575 | B2 | 10/2021 | Trager et al. |
| 11,253,547 | B2 | 2/2022 | Trager et al. |
| 11,365,236 | B2 | 6/2022 | Leong et al. |
| 11,560,548 | B2 | 1/2023 | Campana et al. |
| 11,673,937 | B2 | 6/2023 | Campana et al. |
| 11,873,512 | B2 | 1/2024 | Campana et al. |

(Continued)

FOREIGN PATENT DOCUMENTS

| | | | |
|---|---|---|---|
| CN | 107636015 | A | 1/2018 |
| CN | 107709548 | A | 2/2018 |

(Continued)

OTHER PUBLICATIONS

Aagaard et al., "RNAi therapeutics: Principles, prospects and challenges," Advanced Drug Delivery Reviews, 59 (2007) 75-86 (Year: 2007).
Atreya, et al., "Blockade of interleukin 6 trans signaling suppresses T-cell resistance against apoptosis in chronic intestinal inflammation: Evidence in Crohn disease and experimental colitis in vivo" Nature Medicine, vol. 6, No. 5, May 2000; pp. 583-588.
Auerbach et al., "Angiogenesis assays: Problems and pitfalls," Cancer and Metastasis Reviews, 2000, 19: 167-172 (Year: 2000).
Barrett, et al., "Interleukin 6 is not Made by Chimeric Antigen Receptor T Cells and Does not Impact Their Function" Blood (2016) 128(22):654.

(Continued)

*Primary Examiner* — Julie Wu
(74) *Attorney, Agent, or Firm* — Hamilton, Brook, Smith & Reynolds, P.C.

(57) ABSTRACT

The invention relates to an in vivo functional ligands (IFLs) including a single-chain variable fragment (scFv) domain, a fragment crystallizable (Fc) domain, and a hinge domain joining the scFv and Fc domains. The IFLs specifically bind target receptors and are capable of triggering antibody-dependent cell cytotoxicity (ADCC), antibody-dependent cell phagocytosis (ADCP) and complement-dependent cytotoxicity (CDC), as well as cytokine stimulation. The IFLs may be joined to a chimeric antigen receptor via a self-cleaving peptide. The IoLs may be expressed in immune cells, such as a natural killer cell or a T lymphocyte. Vectors, host cells, and methods of making IFLs are also described.

3 Claims, 14 Drawing Sheets

Specification includes a Sequence Listing.

(56) References Cited

U.S. PATENT DOCUMENTS

| | | | | |
|---|---|---|---|---|
| 11,896,616 | B2 | 2/2024 | Kamiya et al. | |
| 12,258,381 | B2 | 3/2025 | Seow | |
| 12,441,787 | B2 | 10/2025 | Tan et al. | |
| 2003/0129649 | A1 | 7/2003 | Kobilka et al. | |
| 2008/0177047 | A1 | 7/2008 | Fujita-Yamaguchi | |
| 2008/0299137 | A1 | 12/2008 | Svendsen | |
| 2009/0281035 | A1 | 11/2009 | Spee et al. | |
| 2010/0029749 | A1 | 2/2010 | Zhang et al. | |
| 2013/0072401 | A1 | 3/2013 | Ye et al. | |
| 2015/0139943 | A1 | 5/2015 | Campana et al. | |
| 2016/0000828 | A1 | 1/2016 | Campana et al. | |
| 2016/0362472 | A1 | 12/2016 | Bitter et al. | |
| 2017/0051035 | A1* | 2/2017 | Payne | A61K 40/4211 |
| 2017/0073638 | A1 | 3/2017 | Campana et al. | |
| 2017/0129967 | A1 | 5/2017 | Wels et al. | |
| 2017/0368098 | A1 | 12/2017 | Chen et al. | |
| 2018/0002397 | A1 | 1/2018 | Shah | |
| 2018/0044417 | A1 | 2/2018 | Pule et al. | |
| 2018/0371052 | A1 | 12/2018 | Ma et al. | |
| 2019/0062430 | A1 | 2/2019 | Wu et al. | |
| 2019/0290693 | A1 | 9/2019 | Qi et al. | |
| 2019/0336533 | A1* | 11/2019 | Hwang | C07K 14/70578 |
| 2020/0016208 | A1 | 1/2020 | Kamiya et al. | |
| 2020/0255803 | A1 | 8/2020 | Zhang et al. | |
| 2020/0340995 | A1 | 10/2020 | Campana et al. | |
| 2020/0407686 | A1 | 12/2020 | Campana et al. | |
| 2021/0009951 | A1 | 1/2021 | Hu et al. | |
| 2021/0017271 | A1 | 1/2021 | Tan et al. | |
| 2021/0046115 | A1 | 2/2021 | Seow et al. | |
| 2021/0054409 | A1 | 2/2021 | Zhu et al. | |
| 2021/0324388 | A1 | 10/2021 | Vinanica et al. | |
| 2021/0338727 | A1 | 11/2021 | Trager et al. | |
| 2021/0363218 | A1 | 11/2021 | Fan et al. | |
| 2022/0002424 | A1 | 1/2022 | Trager et al. | |
| 2022/0047635 | A1 | 2/2022 | Liu et al. | |
| 2022/0233590 | A1 | 7/2022 | Trager et al. | |
| 2022/0233593 | A1 | 7/2022 | Trager et al. | |
| 2022/0411754 | A1 | 12/2022 | Trager et al. | |
| 2023/0002471 | A1 | 1/2023 | Leong et al. | |
| 2023/0028399 | A1 | 1/2023 | Rajangam et al. | |
| 2023/0220343 | A1 | 7/2023 | Campana et al. | |
| 2023/0265390 | A1 | 8/2023 | Trager et al. | |
| 2023/0390392 | A1 | 12/2023 | Trager et al. | |

FOREIGN PATENT DOCUMENTS

| | | | | | |
|---|---|---|---|---|---|
| CN | 107827990 | A | | 3/2018 | |
| CN | 108840930 | A | | 11/2018 | |
| CN | 109957017 | | * | 7/2019 | |
| CN | 112055717 | B1 | | 4/2024 | |
| EP | 1 036 327 | B1 | | 7/2009 | |
| EP | 3690033 | A1 | | 8/2020 | |
| WO | WO 92/17198 | A1 | | 10/1992 | |
| WO | WO 00/23573 | A2 | | 4/2000 | |
| WO | WO 02/077029 | A2 | | 10/2002 | |
| WO | 2006119115 | A2 | | 11/2006 | |
| WO | WO 2011/069019 | A2 | | 6/2011 | |
| WO | WO-2013059593 | A1 | * | 4/2013 | A61K 38/465 |
| WO | WO 2014/117121 | A1 | | 7/2014 | |
| WO | WO 2015/193411 | A1 | | 12/2015 | |
| WO | 2016/012613 | A1 | | 1/2016 | |
| WO | 2016014576 | A1 | | 1/2016 | |
| WO | 2016/073755 | A9 | | 5/2016 | |
| WO | 2016/100985 | A2 | | 6/2016 | |
| WO | 2017/040324 | A1 | | 8/2016 | |
| WO | WO 2016/126213 | A1 | | 8/2016 | |
| WO | WO 2016/142314 | A1 | | 9/2016 | |
| WO | WO 2017/027325 | A1 | | 2/2017 | |
| WO | WO 2017/079694 | A2 | | 5/2017 | |
| WO | WO-2017161353 | A1 | * | 9/2017 | A61P 35/00 |
| WO | WO 2017/172981 | A2 | | 10/2017 | |
| WO | 2017/186928 | A1 | | 11/2017 | |
| WO | WO-2017222593 | A1 | * | 12/2017 | C07K 16/2812 |
| WO | WO 2018/022646 | A1 | | 2/2018 | |
| WO | 2018/057915 | A1 | | 3/2018 | |
| WO | WO 2018/103503 | A1 | | 6/2018 | |
| WO | WO-2018124766 | A2 | * | 7/2018 | C07K 16/283 |
| WO | 2018/146317 | A1 | | 8/2018 | |
| WO | WO-2018211244 | A1 | * | 11/2018 | C07K 16/283 |
| WO | WO-2019010224 | A1 | * | 1/2019 | A61K 35/17 |
| WO | WO 2019/028051 | A1 | | 2/2019 | |
| WO | 2019/077037 | A1 | | 4/2019 | |
| WO | WO 2019/062817 | A1 | | 4/2019 | |
| WO | 2019/112899 | A2 | | 6/2019 | |
| WO | 2019/129220 | A1 | | 7/2019 | |
| WO | WO 2019/129002 | A1 | | 7/2019 | |
| WO | WO 2019/155286 | A2 | | 8/2019 | |
| WO | WO 2019/155288 | A1 | | 8/2019 | |
| WO | 2019/199689 | A1 | | 10/2019 | |
| WO | WO 2020/083282 | A1 | | 4/2020 | |
| WO | WO 2021/009694 | A1 | | 1/2021 | |

OTHER PUBLICATIONS

Beans, "Targeting metastasis to halt cancer's spread," PNAS 2018; 115(50): 12539-12543 (Year: 2018).

Bedouelle, et al., "Diversity and junction residues as hotspots of binding energy in an antibody neutralizing the dengue virus" FEBS Journal 273 (2006) 34-46.

Berger, C. et al., "CD28 costimulation and immunoaffinity-based selection efficiently gernate primary gene-modified T cells for adoptive immunotherapy," Blood, 101: 476-484 (2003).

Berger, C. et al., "Safety and immunologic effects of IL-15 administration in nonhuman primates," Blood, 114(12): 2417-2426 (2009).

Blumberg et al., "Unraveling the autoimmune translational research process layer by layer," (Nat Med.; 18(1): 35-41) (Year: 2015).

Bork, "Powers and Pitfalls in Sequence Analysis: The 70% Hurdle," Genome Research, 2000, 10:398-400 (Year: 2000).

Brentjens, et al., "Eradication of systemic B-cell tumors by genetically targeted human T lymphocytes co-stimulated by CD80 and interleukin-15" Nat. Med. 2003; 9(3):279-286.

Brown, et al., "Tolerance to Single, but not Multiple, Amino Acid Replacements in Antibody VH CDR2" J. Immunol. May 1, 1996; 156(9):3285-91.

Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue" J. Cell Biol. 111 :2129-2138, 1990 (Year: 1990).

Call et al., "The structural basis for intramembrane assembly of an activating immunoreceptor complex" Nat Immunol Nov. 2010; 11(11): 1023-1029.

Colman, "Effects of amino acid sequence changes on antibody-antigen interactions" Research in Immunology 145:33-36 (1994).

Cooper, et al., "T-cell clones can be rendered specific for CD 19: toward the selective augmentation of the graft- versus-B-lineage leukemia effect" Blood 2003; 101(4):1637-1644.

Eshhar et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci. USA, 1993, 90:720-724.

Figueiredo et al., "Permanent silencing of NKG2A expression for cell-based therapeutics" J. Mol. Med. (2009) 87:199-210.

Gravanis et al., "The changing world of cancer drug development: the regulatory bodies' perspective," Chin Clin Oneal, 2014, 3, pp. 1-5 (Year: 2014).

Greenspan et al., "Defining epitopes: It's not as easy as it seems" Nature Biotechnology, 17:936-937 (Year: 1999).

Grupp et al., "Chimeric antigen receptor-modified T cells for acute lymphoid leukemia," N Engl J Med. Apr. 18, 2013; 368 (16):1509-1518.

Gura T, "Systems for Identifying New Drugs are Often Faulty," Science 1997, 278(5340): 1041-1042 (Year: 1997).

Hait., "Anticancer drug development: the grand challenges," Nature Reviews/Drug Discovery, 2010, 9, pp. 253-254 (Year: 2010).

Heppner et al., "Tumor heterogeneity: biological implications and therapeutic consequences," 1983, Cancer Metastasis Reviews 2:5-23 (Year: 1983).

(56) References Cited

OTHER PUBLICATIONS

Imai C, et al., "Chimeric receptors with 4-1BB signaling capacity provoke potent cytotoxicity against acute lymphoblastic leukemia", Leukemia., Feb. 12, 2004; 18(4):676-684.
Hong, et al., "Interleukin-6 expands homeostatic space for peripheral T cells" Cytokine 64 (2013) pp. 532-540.
Hu, et al., "Gene Therapy of Malignant Solid Tumors by Targeting erbB2 Receptors and by Activating T Cells" Cancer Biotherapy and Radiopharmaceuticals, vol. 27, No. 10, 2012.
Jain RK, "Barriers to Drug Delivery in Solid Tumors," 1994, Scientific American, pp. 58-645 (Year: 1994).
Jiang, Z., et al., "IL-6 trans-signaling promotes the expansion and anti-tumor activity of Car T cells" Leukemia (2021) 35; pp. 1380-1391.
Kulmanov et al., "DeepGO: predicting protein functions from sequence and interactions using a deep ontology-aware classifier," Bioinformatics, 34(4), 2018, 660-668 (Year: 2018).
Lazar et al., "Transforming Growth Factor • : Mutation of Aspartic Acid 47 and Leucine 48 Results in Different Biological Activities" Mol. Cell. Biol., vol. 8, No. 3, 1247-1252, 1988 (Year: 1988).
Lee et al., "Current concepts in the diagnosis and management of cytokine release syndrome" Blood, Jul. 10, 2014, vol. 124, No. 2, 188-195.
Li, et al., "IL-6 Promotes T Cell Prolif era ti on and Expansion under Inflammatory Conditions in Association with Low- Level ROR-yt Expression" J. Immunol (2018) 201(10); pp. 2934-2946.
McKeague, et al., "Challenges and Opportunities for Small Molecule Aptamer Development," Review Article, Journal of Nucleic Acids, vol. 2012, Article ID 748913.
Miosge, "Comparison of predicted and actual consequences of missense mutations," Proc Natl Acad Sci USA Sep. 15, 2015;112(37):E5189-98 (Year: 2015).
Morgan, et al., "Case Report of a Serious Adverse Event Following the Administration of T Cells Transduced With a Chimeric Antigen Receptor Recognizing ERBB2" Molecular Therapy, vol. 18, No. 4, 843-851, Apr. 2010.
Nish, et al., "T cell-intrinsic role of IL-6 signaling in primary and memory responses" eLife 2014;3:e01949.
Pelechas et al., "Sirukumab: a promising therapy for rheumatoid arthritis" Expert Opinion on Biological Therapy, 2017, vol. 17, No. 6, 755-763.
Qin et al., "Incorporation of a hinge domain improves the expansion of chimeric antigen receptor T cells" J. Hematol. Oneal. Mar. 13, 2017; 10(1):68.
Rochman, et al., "IL-6 Increases Primed Cell Expansion and Survival" The Journal of Immunology (2005) 174(8); pp. 4761-4767.
Rudikoff, et al., "Single amino acid substitution altering antigen-binding specificity " Proc. Natl Acad. Sci. USA, vol. 79, pp. 1979-1983, Mar. 1982.
Skolnick et al., "From genes to protein structure and function: novel applications of computational approaches in the genomic era," Trends Biotechnol. Jan. 2000; 18(1 ):34-9 (Year: 2000).
Sporn et al., "Chemoprevention of Cancer," Carcinogenesis, vol. 21, No. 3 (2000), 525-530 (Year: 2000).
Teachey, et al., "Identification of Predictive Biomarkers for Cytokine Release Syndrome after Chimeric Antigen Receptor T-cell Therapy for Acute Lymphoblastic Leukemia" Cancer Discovery, Jun. 2016, pp. 664-679.
Torok et al., "Pharmacogenetics of Crohn's disease," Pharmacogenomics (2008) 9(7), 881-893 (Year: 2008).
Vajdos, et al., "Comprehensive Functional Maps of the Antige••binding Site of an Anti-Erb82 Antibody Obtained with Shotgun Scanning Mutagenesis" J. Mol. Biol. (2002) 320, 415-428.
Warzocha et al., "Antisense Strategy: Biological Utility and Prospects in the Treatment of Hematological Malignancies," Leukemia and Lymphoma (1997) vol. 24. pp. 267-281 (Year: 1997).
Yan et al., "HER2 expression status in diverse cancers: review of results from 37,992 patients," Cancer Metastasis Rev (2015) 34:157-164 (Year: 2015).
International Search Report and Written Opinion for Int'l Application No. PCT/IB2020/056659, titled, "Functional Binders Synthesized and Secreted by Immune Cells," Date Mailed: Nov. 2, 2020.
International Preliminary Report on Patentability issued on Jan. 27, 2022 for International Application No. PCT/IB2020/056659, entitled "Functional Binders Synthesized and Secreted by Immune Cells".
Brand, L.J. et al., "Abstract LB-185: A PSMA-directed natural killer cell approach for prostate cancer immunotherapy," Cancer Research, 77(13 Supplement): Abstract No. LB-185, 1-4 (Jul. 2017).
Bridgeman, J.S. et al., "The Optimal Antigen Response of Chimeric Antigen Receptors Harboring the CD35 Transmembrane Domain is Dependent upon Incorporation of the Receptor into the Endogenous TCR/CD3 Complex," J Immunol, 184(12): 6938-6949 (May 2010).
Caratelli et al., "FCy Chimeric Receptor-Engineered T Cells: Methodology, Advantages, Limitations, and Clinical Relevance," Front Immunol., vol. 8, Article 457 , 8 pages (Apr. 27, 2017).
Chen, F., "Construction of Anti-CD20 Single-Chain Antibody-CD28-CD137-TCR Recombinant Genetic Modified T Cells and its Treatment Effect on B Cell Lymphoma," Med Sci Monit 2015; 21:2110-2115 (Jul. 21, 2015).
Galustian, C. et al., "MP84-07A Tale of Tails—A Novel Approach to Immunotherapy of Prostate Cancer," J Urol, 195(4S): e1092 (May 2016).
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).
Hurton, L.V. et al., "Tethered IL-15 augments antitumor activity and promotes a stem-cell memory subset in tumor-specific T cells," PNAS, USA, 113(48): E7788-E7797 (Nov. 2016).
Imai C et al. "Genetic modification of primary natural killer cells overcomes inhibitory signals and induces specific killing of leukemic cells," Blood. 2005; 106:376-383.
Kaiser, B.K. et al., "Structural basis for NKG2A/CD94 Recognition of HLA-E," Proc Nat'l Acad Sci USA, 105(18): 6696-6701 (Apr. 2008).
Kober, J., et al. "The capacity of the TNF family members 4-1BBL, OX40L, CD70, Gitrl, CD30L and LIGHT to costimulate human T cells," Eur J Immuno, vol. 38, No. 10, pp. 2678-2688 (Oct. 28, 2008).
Kochenderfer, J.N., "Eradication of B-lineage and regression of lymphoma in a patient treated with autologous T cells genetically engineered to recognize CD19," Blood, 2010, 116(20), 4099-4102.
Kohrt, H.E., "Immunomodulation of NK Cells through 4-1BB (CD137) to Improve the Anti-Lymphoma Activity of Rituximab: Antibody-Based Anti-Lymphoma Snergy," Blood, 2010, 116(21), 422.
LaBonte, M.L. et al., "Molecular Determinants Regulating the Pairing of NKG2 Molecules with CD94 for Cell Surface Heterodimer Expression," J Immunol, 172(11): 6902-6912 (May 2004).
Lanier, Lewis L., "NK Cell Recognition," Annual Review of Immunology, vol. 23, No. 1, pp. 225-274 (2005).
Mirzaei, H.R., et al., "Construction and functional characterization of a fully human anti-CD19 chimeric antigen receptor (huCAR)-expressing primary human T cells," J Cell Physiol. Jun. 2019; 234(6):9207-9215. doi: 10.1002/jcp.27599. Epub Oct. 26, 2018. PMID: 30362586 (Abstract).
Robak, T., New Anti-CD20 Monoclonal Antibodies for the Treatment of B-Cell Lymphoid Malignancies, BioDrugs 25, 13-25 (2011) (Abstract).
Schmohl J.U., et al., Tetraspecific scFv construct provides NK cell mediated ADCC and self-sustaining stimuli via insertion of IL-15 as a cross-linker. Oncotarget. 2016; 7: 73830-73844. Retrieved from https://www.oncotarget.com/article/12073/ (Abstract).
Sullivan, L.C. et al., "The Heterodimeric Assembly of the CD94-NKG2 Receptor Family and Implications for Human Leukocyte Antigen-E Recognition," Immunity, 27(6): 900-911 (Dec. 2007).
Wang, W., "NK cell-mediated antibody-dependent cellular cytotoxicity in cancer immunotherapy," Frontiers in Immunology, 2015, 6, 368.
Zah, E. et al., "T Cells Expressing CD19/CD20 Bispecific Chimeric Antigen Receptors Prevent Antigen Escape by Malignant B Cells," Cancer Immunol Res, 4(6): 498-508 (Apr. 2016).

(56) References Cited

OTHER PUBLICATIONS

Barrett, D., "IL-6 Blockade in Cytokine Storm Syndromes," Ch. 27 in Cytokine Storm Syndrome, Second Edition, Advances in Experimental Medicine and Biology 1448 (Cron and Behrens, Eds. 2024).
Behrens, et al., "Anti-Interferon-γ Therapy for Cytokine Storm Syndromes," Ch. 28 in Cytokine Storm Syndrome, Second Edition, Advances in Experimental Medicine and Biology 1448 (Cron and Behrens, Eds. 2024).
Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).
Gardner, et al., "Preemptive mitigation of CD19 Car T-cell cytokine release syndrome without attenuation of antileukemic efficacy," blood, Dec. 12, 2019, vol. 134, No. 24, pp. 2149-2158.
Kadauke, et al., "Risk-Adapted Preemptive Tocilizumab to Prevent Severe Cytokine Release Syndrome After CTL019 for Pediatric B-Cell Acute Lymphoblastic Leukemia: A Prospective Clinical Trial," Journal of Clinical Oncology, vol. 39, Issue 8, pp. 920-931, 2021.
Lanier L.L., "DAP10- and DAP12-associated receptors in innate immunity;" Immunol Rev. Jan. 2009;227(1): 150-60. doi: 10.1111/j.1600-065X.2008.00720.x. PMID: 19120482; PMCID: PMC2794881. (Year: 2009).
Locke, et al., "Preliminary Results of Prophylactic Tocilizumab after Axicabtageneciloleucel (axi-cel; KTE-C19) Treatment for Patients with Refractory, Aggressive Non-Hodgkin Lymphoma (NHL)," Blood blood (2017) 130 (Suppl_1):1547.
Miyake, et al., "IL-6 receptor antibody treatment improves muscle weakness in experimental autoimmune myasthenia gravis mouse model," Frontiers in Neurology, May 1, 2024.
Murthy et al., "Cytokine Release Syndrome: Current Perspectives," Immuno Targets and Therapy, 2019:8, 43-52.
Neelapu, et al., "Chimeric antigen receptor T-cell therapy—assessment and management of toxicities," Nature Reviews, Clinical Oncology, vol. 15, Jan. 2018.
Speake, et al., "IL-6-targeted therapies to block the cytokine or its receptor drive distinct alterations in T cell function," JCI Insight 2022;7(22):e159436.
Ueda, et al., "Novel genetically-humanized mouse model established to evaluate efficacy of therapeutic agents to human interleukin-6 receptor," Scientific Reports, 3:1196, Feb. 1, 2013.
UniProt P26717 NKG2C_HUMAN. Integrated into UniProtKB/Swiss-Prot Aug. 1, 1992. https://www.uniprot.org/uniprotkb/P26717/ entry. Accessed Jul. 17, 2024 (Year: 1992).
Imamura, M. et al., "Autonomous growth and increased cytotoxicity of natural killer cells expressing membrane-bound interleukin-15," Blood, 124(7): 1081-1088 (2014).
Suarez, et al., "Chimeric Antigen Receptor T Cells Secreting Anti-PD-L1 Antibodies More Effectively Regress Renal Cell Carcinoma in a Humanized Mouse Model," Oncotarget, vol. 7, No. 23, Apr. 29, 2016.
Li, et al., "Therapeutically Targeting Glypican-2 via Single-Domain Antibody-Based Chimeric Antigen Receptors and Immunotoxins in Neuroblasoma," PNAS, pp. E6623-E6631 (Jul. 24, 2017).
Zuther, "Generation of the Plasmid pMT/BiP SCA431scFv-Fc-IL 15 (#1118)," Chapter 4.1.8 of an Anti-CD30 Immunocytokine with Combined IL-2 and IL-12 Domains Enhances Anti-Tumor Immunity, p. 70 (Oct. 1, 2009).
Chen, et al., Fusion protein linkers: Property, design and functionality, Sep. 29, 2012, Advanced Drug Delivery Reviews, 1357-1369, 65.
Cesco-Gaspere et al., "Immunomodulation in the treatment of haematological malignancies", Clinical and Experimental Medicine, vol. 9, 2009, pp. 81-92.
Ibrahimi et al., "Highly Efficient Multicistronic Lentiviral Vectors with Peptide 2A Sequences", Human Gene Therapy, vol. 20, No. 8, Jun. 11, 2009, 845-860, 19 pages.
Mirzaei et al., "Chimeric Antigen Receptors T Cell Therapy in Solid Tumor: Challenges and Clinical Applications", Front. Immunol., vol. 8, Dec. 2017, Article 1850, 13 pages.
Yanez et al., "Granulocyte-monocyte progenitors and monocyte dendritic cell progenitors independently produce functionally distinct monocytes," Immunity 47(5), 890-902, Nov. 21, 2017. (Year: 2017).

* cited by examiner

SEQUENCE LISTING

```
<160> NUMBER OF SEQ ID NOS: 54

<210> SEQ ID NO 1
<211> LENGTH: 48
<212> TYPE: DNA
<213> ORGANISM: Artificial Sequence
<220> FEATURE:
<223> OTHER INFORMATION: Anti-CD20 IFL, Rituximab signal peptide; cDNA

<400> SEQUENCE: 1

atggacttcc aggtgcagat catcagcttt ctgctgatct ccgcctct                48


<210> SEQ ID NO 2
<211> LENGTH: 16
<212> TYPE: PRT
<213> ORGANISM: Artificial Sequence
<220> FEATURE:
<223> OTHER INFORMATION: Anti-CD20 IFL, Rituximab signal peptide; amino
      acid

<400> SEQUENCE: 2

Met Asp Phe Gln Val Gln Ile Ile Ser Phe Leu Leu Ile Ser Ala Ser
1               5                   10                  15


<210> SEQ ID NO 3
<211> LENGTH: 336
<212> TYPE: DNA
<213> ORGANISM: Artificial Sequence
<220> FEATURE:
<223> OTHER INFORMATION: Anti-CD20 IFL, Immunoglobulin variable domain
      of rituximab light chain; cDNA
```

<400> SEQUENCE: 3

```
gtgatcatgt ccaggggcca gatcgtgctg agccagtccc cagcaatcct gtctgccagc     60

cctggagaga aggtgaccat gacatgccgc gccagctcct ctgtgagcta catccactgg    120

ttccagcaga agcccggcag ctcccctaag ccctggatct atgccacaag caacctggcc    180

tccggcgtgc ctgtgcggtt ttccggctct ggcagcggca cctcctactc tctgacaatc    240

agcagagtgg aggccgagga tgccgccacc tactattgcc agcagtggac ctccaatccc    300

cctacattcg gcggcggcac caagctggag atcaag                              336
```

<210> SEQ ID NO 4
<211> LENGTH: 112
<212> TYPE: PRT
<213> ORGANISM: Artificial Sequence
<220> FEATURE:
<223> OTHER INFORMATION: Anti-CD20 IFL, Immunoglobulin variable domain of rituximab light chain; amino acid

<400> SEQUENCE: 4

```
Val Ile Met Ser Arg Gly Gln Ile Val Leu Ser Gln Ser Pro Ala Ile
1               5                   10                  15

Leu Ser Ala Ser Pro Gly Glu Lys Val Thr Met Thr Cys Arg Ala Ser
            20                  25                  30

Ser Ser Val Ser Tyr Ile His Trp Phe Gln Gln Lys Pro Gly Ser Ser
        35                  40                  45

Pro Lys Pro Trp Ile Tyr Ala Thr Ser Asn Leu Ala Ser Gly Val Pro
    50                  55                  60

Val Arg Phe Ser Gly Ser Gly Ser Gly Thr Ser Tyr Ser Leu Thr Ile
65                  70                  75                  80

Ser Arg Val Glu Ala Glu Asp Ala Ala Thr Tyr Tyr Cys Gln Gln Trp
                85                  90                  95

Thr Ser Asn Pro Pro Thr Phe Gly Gly Gly Thr Lys Leu Glu Ile Lys
            100                 105                 110
```

<210> SEQ ID NO 5
<211> LENGTH: 45
<212> TYPE: DNA
<213> ORGANISM: Artificial Sequence
<220> FEATURE:
<223> OTHER INFORMATION: Anti-CD20 IFL, Linker; cDNA

<400> SEQUENCE: 5

```
ggcggcggcg gctctggagg aggaggcagc ggcggaggag gctcc                     45
```

<210> SEQ ID NO 6
<211> LENGTH: 15
<212> TYPE: PRT
<213> ORGANISM: Artificial Sequence
<220> FEATURE:
<223> OTHER INFORMATION: Anti-CD20 IFL, Linker; amino acid

<400> SEQUENCE: 6

```
Gly Gly Gly Gly Ser Gly Gly Gly Gly Ser Gly Gly Gly Gly Ser
1               5                   10                  15
```

<210> SEQ ID NO 7
<211> LENGTH: 363
<212> TYPE: DNA
<213> ORGANISM: Artificial Sequence
<220> FEATURE:
<223> OTHER INFORMATION: Anti-CD20 IFL, Immunoglobulin variable domain of rituximab heavy chain; cDNA

<400> SEQUENCE: 7
caggtgcagc tgcagcagcc aggagcagag ctggtgaagc caggagcctc tgtgaagatg 60
agctgtaagg cctccggcta caccttcaca agctataaca tgcactgggt gaagcagaca 120
ccaggaaggg gcctggagtg gatcggagca atctaccctg gcaacggcga cacctcctat 180
aatcagaagt ttaagggcaa ggccaccctg acagccgata agtctagctc cacagcctac 240
atgcagctgt ctagcctgac ctctgaggac agcgccgtgt actattgcgc cagaagcaca 300
tactatggcg gcgattggta cttcaacgtg tggggagcag gcaccacagt gaccgtgtct 360
gcc 363

<210> SEQ ID NO 8
<211> LENGTH: 121
<212> TYPE: PRT
<213> ORGANISM: Artificial Sequence
<220> FEATURE:
<223> OTHER INFORMATION: Anti-CD20 IFL, Immunoglobulin variable domain of rituximab heavy chain; amino acid

<400> SEQUENCE: 8

Gln Val Gln Leu Gln Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Asn Met His Trp Val Lys Gln Thr Pro Gly Arg Gly Leu Glu Trp Ile
35 40 45

Gly Ala Ile Tyr Pro Gly Asn Gly Asp Thr Ser Tyr Asn Gln Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Ser Thr Tyr Tyr Gly Gly Asp Trp Tyr Phe Asn Val Trp Gly
100 105 110

Ala Gly Thr Thr Val Thr Val Ser Ala
115 120

<210> SEQ ID NO 9
<211> LENGTH: 699
<212> TYPE: DNA
<213> ORGANISM: Artificial Sequence
<220> FEATURE:
<223> OTHER INFORMATION: Anti-CD20 IFL, Hinge and constant heavy domain 2 and 3 of immunoglobulin G1; cDNA

<400> SEQUENCE: 9
gagccaaaga gctgtgacaa gacccacaca tgcccaccat gtccagcacc tgagctgctg 60
ggaggacctt ccgtgttcct gtttcctcca aagccaaagg ataccctgat gatctctagg 120
acccctgagg tgacatgcgt ggtggtggac gtgagccacg aggaccccga ggtgaagttt 180
aactggtacg tggacggcgt ggaggtgcac aatgccaaga ccaagcctcg ggaggagcag 240
tacaactcca catatagagt ggtgtctgtg ctgaccgtgc tgcaccagga ttggctgaac 300
ggcaaggagt ataagtgcaa ggtgtccaat aaggccctgc cagcccccat cgagaagaca 360
atctctaagg ccaagggcca gcctagggag ccacaggtgt acaccctgcc accttcccgc 420
gacgagctga caaagaacca ggtgtctctg acctgtctgg tgaagggctt ctatccatct 480

-continued

```
gacatcgccg tggagtggga gagcaatggc cagcccgaga acaattacaa gaccacacca    540

cccgtgctgg actccgatgg ctctttcttt ctgtatagca agctgacagt ggacaagtcc    600

cggtggcagc agggcaacgt gtttagctgt tccgtgatgc acgaggccct gcacaatcac    660

tacacccaga agtctctgag cctgtccccc ggcaagtga                           699
```

<210> SEQ ID NO 10
<211> LENGTH: 232
<212> TYPE: PRT
<213> ORGANISM: Artificial Sequence
<220> FEATURE:
<223> OTHER INFORMATION: Anti-CD20 IFL, Hinge and constant heavy domain 2 and 3 of immunoglobulin G1; amino acid

<400> SEQUENCE: 10

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 11
<211> LENGTH: 63
<212> TYPE: DNA
<213> ORGANISM: Artificial Sequence
<220> FEATURE:
<223> OTHER INFORMATION: Anti-CD19 IFL, CD8alpha signal peptide; cDNA

<400> SEQUENCE: 11

```
atggccttac cagtgaccgc cttgctcctg ccgctggcct tgctgctcca cgccgccagg     60

ccg                                                                   63
```

<210> SEQ ID NO 12
<211> LENGTH: 21
<212> TYPE: PRT
<213> ORGANISM: Artificial Sequence
<220> FEATURE:
<223> OTHER INFORMATION: Anti-CD19 IFL, CD8alpha signal peptide; amino acid

<400> SEQUENCE: 12

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 13
<211> LENGTH: 321
<212> TYPE: DNA
<213> ORGANISM: Artificial Sequence
<220> FEATURE:
<223> OTHER INFORMATION: Anti-CD19 IFL, Immunoglobulin variable domain of light chain; cDNA

<400> SEQUENCE: 13

```
gacatccaga tgacacagac tacatcctcc ctgtctgcct ctctgggaga cagagtcacc     60

atcagttgca gggcaagtca ggacattagt aaatatttaa attggtatca gcagaaacca    120

gatggaactg ttaaactcct gatctaccat acatcaagat tacactcagg agtcccatca    180

aggttcagtg gcagtgggtc tggaacagat tattctctca ccattagcaa cctggagcaa    240

gaagatattg ccacttactt ttgccaacag ggtaatacgc ttccgtacac gttcggaggg    300

gggaccaagc tggagatcac a                                              321
```

<210> SEQ ID NO 14
<211> LENGTH: 107
<212> TYPE: PRT
<213> ORGANISM: Artificial Sequence
<220> FEATURE:
<223> OTHER INFORMATION: Anti-CD19 IFL, Immunoglobulin variable domain of light chain; amino acid

<400> SEQUENCE: 14

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

<210> SEQ ID NO 15
<211> LENGTH: 45
<212> TYPE: DNA
<213> ORGANISM: Artificial Sequence
<220> FEATURE:
<223> OTHER INFORMATION: Anti-CD19 IFL, Linker; cDNA

<400> SEQUENCE: 15
ggtggcggtg gctcgggcgg tggtgggtcg ggtggcggcg gatct 45

<210> SEQ ID NO 16
<211> LENGTH: 15
<212> TYPE: PRT
<213> ORGANISM: Artificial Sequence
<220> FEATURE:
<223> OTHER INFORMATION: Anti-CD19 IFL, Linker; amino acid

<400> SEQUENCE: 16

Gly Gly Gly Gly Ser Gly Gly Gly Gly Ser Gly Gly Gly Gly Ser
1 5 10 15

<210> SEQ ID NO 17
<211> LENGTH: 360
<212> TYPE: DNA
<213> ORGANISM: Artificial Sequence
<220> FEATURE:
<223> OTHER INFORMATION: Anti-CD19 IFL, Immunoglobulin variable domain of heavy chain; cDNA

<400> SEQUENCE: 17
gaggtgaaac tgcaggagtc aggacctggc ctggtggcgc cctcacagag cctgtccgtc 60
acatgcactg tctcaggggt ctcattaccc gactatggtg taagctggat tcgccagcct 120
ccacgaaagg gtctggagtg gctgggagta atatggggta gtgaaaccac atactataat 180
tcagctctca aatccagact gaccatcatc aaggacaact ccaagagcca agttttctta 240
aaaatgaaca gtctgcaaac tgatgacaca gccatttact actgtgccaa acattattac 300
tacggtggta gctatgctat ggactactgg ggccaaggaa cctcagtcac cgtctcctca 360

<210> SEQ ID NO 18
<211> LENGTH: 120
<212> TYPE: PRT
<213> ORGANISM: Artificial Sequence
<220> FEATURE:
<223> OTHER INFORMATION: Anti-CD19 IFL, Immunoglobulin variable domain of heavy chain; amino acid

<400> SEQUENCE: 18

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser
115 120

<210> SEQ ID NO 19
<211> LENGTH: 699
<212> TYPE: DNA

```
<213> ORGANISM: Artificial Sequence
<220> FEATURE:
<223> OTHER INFORMATION: Anti-CD19 IFL, Hinge and constant heavy domain
      2 and 3 of immunoglobulin G1; cDNA

<400> SEQUENCE: 19

gagccaaaga gctgtgacaa gacccacaca tgcccaccat gtccagcacc tgagctgctg     60

ggaggacctt ccgtgttcct gtttcctcca aagccaaagg ataccctgat gatctctagg    120

acccctgagg tgacatgcgt ggtggtggac gtgagccacg aggaccccga ggtgaagttt    180

aactggtacg tggacggcgt ggaggtgcac aatgccaaga ccaagcctcg ggaggagcag    240

tacaactcca catatagagt ggtgtctgtg ctgaccgtgc tgcaccagga ttggctgaac    300

ggcaaggagt ataagtgcaa ggtgtccaat aaggccctgc cagcccccat cgagaagaca    360

atctctaagg ccaagggcca gcctagggag ccacaggtgt acaccctgcc accttcccgc    420

gacgagctga caaagaacca ggtgtctctg acctgtctgg tgaagggctt ctatccatct    480

gacatcgccg tggagtggga gagcaatggc cagcccgaga acaattacaa gaccacacca    540

cccgtgctgg actccgatgg ctctttcttt ctgtatagca agctgacagt ggacaagtcc    600

cggtggcagc agggcaacgt gtttagctgt tccgtgatgc acgaggccct gcacaatcac    660

tacacccaga agtctctgag cctgtccccc ggcaagtga                           699


<210> SEQ ID NO 20
<211> LENGTH: 232
<212> TYPE: PRT
<213> ORGANISM: Artificial Sequence
<220> FEATURE:
<223> OTHER INFORMATION: Anti-CD19 IFL, Hinge and constant heavy domain
      2 and 3 of immunoglobulin G1; amino acid

<400> SEQUENCE: 20

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
```

-continued

```
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 21
<211> LENGTH: 48
<212> TYPE: DNA
<213> ORGANISM: Artificial Sequence
<220> FEATURE:
<223> OTHER INFORMATION: Anti-CD20 IFL-P2A-CD16V-BB-zeta, Rituximab
      signal peptide; cDNA

<400> SEQUENCE: 21

atggatttcc aggtccagat tatttccttc ctgctgatta gtgccagt                  48


<210> SEQ ID NO 22
<211> LENGTH: 16
<212> TYPE: PRT
<213> ORGANISM: Artificial Sequence
<220> FEATURE:
<223> OTHER INFORMATION: Anti-CD20 IFL-P2A-CD16V-BB-zeta, Rituximab
      signal peptide; amino acid

<400> SEQUENCE: 22

Met Asp Phe Gln Val Gln Ile Ile Ser Phe Leu Leu Ile Ser Ala Ser
1               5                   10                  15


<210> SEQ ID NO 23
<211> LENGTH: 339
<212> TYPE: DNA
<213> ORGANISM: Artificial Sequence
<220> FEATURE:
<223> OTHER INFORMATION: Anti-CD20 IFL-P2A-CD16V-BB-zeta, Immunoglobulin
      variable domain of rituximab light chain; cDNA

<400> SEQUENCE: 23

gtgattatga gtagaggcca gattgtgctg agccagtccc cagcaatcct gagcgcctcc     60

ccaggagaga aggtgacaat gacctgcaga gccagctcct ctgtgagcta catccactgg    120

ttccagcaga agcccggcag ctccccaaag ccctggatct atgccacctc caacctggcc    180

tctggcgtgc ctgtgagatt ttctggcagc ggctccggca catcttacag cctgaccatc    240

agcagggtgg aggcagagga cgcagcaacc tactattgcc agcagtggac atccaatccc    300

cctaccttcg gcggcggcac aaagctggag atcaagggc                           339


<210> SEQ ID NO 24
<211> LENGTH: 112
<212> TYPE: PRT
<213> ORGANISM: Artificial Sequence
<220> FEATURE:
<223> OTHER INFORMATION: Anti-CD20 IFL-P2A-CD16V-BB-zeta, Immunoglobulin
      variable domain of rituximab light chain; amino
      acid

<400> SEQUENCE: 24

Val Ile Met Ser Arg Gly Gln Ile Val Leu Ser Gln Ser Pro Ala Ile
1               5                   10                  15

Leu Ser Ala Ser Pro Gly Glu Lys Val Thr Met Thr Cys Arg Ala Ser
            20                  25                  30

Ser Ser Val Ser Tyr Ile His Trp Phe Gln Gln Lys Pro Gly Ser Ser
        35                  40                  45
```

Pro Lys Pro Trp Ile Tyr Ala Thr Ser Asn Leu Ala Ser Gly Val Pro
    50                  55                  60

Val Arg Phe Ser Gly Ser Gly Ser Gly Thr Ser Tyr Ser Leu Thr Ile
65                  70                  75                  80

Ser Arg Val Glu Ala Glu Asp Ala Ala Thr Tyr Tyr Cys Gln Gln Trp
                85                  90                  95

Thr Ser Asn Pro Pro Thr Phe Gly Gly Gly Thr Lys Leu Glu Ile Lys
            100                 105                 110

<210> SEQ ID NO 25
<211> LENGTH: 42
<212> TYPE: DNA
<213> ORGANISM: Artificial Sequence
<220> FEATURE:
<223> OTHER INFORMATION: Anti-CD20 IFL-P2A-CD16V-BB-zeta, Linker; cDNA

<400> SEQUENCE: 25
ggcggcggct ctggaggagg aggaagcgga ggaggaggct cc 42

<210> SEQ ID NO 26
<211> LENGTH: 15
<212> TYPE: PRT
<213> ORGANISM: Artificial Sequence
<220> FEATURE:
<223> OTHER INFORMATION: Anti-CD20 IFL-P2A-CD16V-BB-zeta, Linker; amino acid

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 363
<212> TYPE: DNA
<213> ORGANISM: Artificial Sequence
<220> FEATURE:
<223> OTHER INFORMATION: Anti-CD20 IFL-P2A-CD16V-BB-zeta, Immunoglobulin variable domain of rituximab heavy chain; cDNA

<400> SEQUENCE: 27
caggtgcagc tgcagcagcc tggagcagag ctggtgaagc caggagccag cgtgaagatg 60
tcctgtaagg cctctggcta cacattcacc agctataaca tgcactgggt gaagcagacc 120
ccaggaagag gcctggagtg gatcggagcc atctaccctg gcaacggcga cacatcctat 180
aatcagaagt ttaagggcaa ggccacactg accgccgata agtctagctc caccgcctac 240
atgcagctgt ctagcctgac atccgaggac tctgccgtgt actattgcgc caggagcacc 300
tactatggcg gcgattggta cttcaacgtg tggggcgccg gcaccacagt gacagtgtct 360
gcc 363

<210> SEQ ID NO 28
<211> LENGTH: 121
<212> TYPE: PRT
<213> ORGANISM: Artificial Sequence
<220> FEATURE:
<223> OTHER INFORMATION: Anti-CD20 IFL-P2A-CD16V-BB-zeta, Immunoglobulin variable domain of rituximab heavy chain; amino acid

<400> SEQUENCE: 28

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr

```
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120


<210> SEQ ID NO 29
<211> LENGTH: 696
<212> TYPE: DNA
<213> ORGANISM: Artificial Sequence
<220> FEATURE:
<223> OTHER INFORMATION: Anti-CD20 IFL-P2A-CD16V-BB-zeta, Hinge and
      constant heavy domain 2 and 3 of immunoglobulin
      G1; cDNA

<400> SEQUENCE: 29

gagcccaaga gctgtgacaa gacacacacc tgcccaccat gtcctgcacc agagctgctg      60

ggaggaccat ccgtgttcct gtttcctcca aagcccaagg ataccctgat gatctctcgc     120

acacctgagg tgacctgcgt ggtggtggac gtgagccacg aggatccaga ggtgaagttt     180

aactggtacg tggacggcgt ggaggtgcac aatgccaaga ccaagcctag agaggagcag     240

tacaacagca cctatagggt ggtgtccgtg ctgacagtgc tgcaccagga ttggctgaac     300

ggcaaggagt ataagtgcaa ggtgtccaat aaggccctgc ccgcccctat cgagaagacc     360

atctctaagg caaagggaca gccaagggag ccacaggtgt acacactgcc ccctagccgg     420

gacgagctga ccaagaacca ggtgtccctg acatgtctgg tgaagggctt ctatccatcc     480

gatatcgccg tggagtggga gtctaatggc cagcccgaga acaattacaa gaccacacca     540

cccgtgctgg acagcgatgg ctccttcttt ctgtattcta agctgaccgt ggacaagagc     600

cggtggcagc agggcaacgt gttctcctgc tctgtgatgc acgaggccct gcacaatcac     660

tacacccaga agagcctgtc cctgtctccc ggcaag                               696


<210> SEQ ID NO 30
<211> LENGTH: 232
<212> TYPE: PRT
<213> ORGANISM: Artificial Sequence
<220> FEATURE:
<223> OTHER INFORMATION: Anti-CD20 IFL-P2A-CD16V-BB-zeta, Hinge and
      constant heavy domain 2 and 3 of immunoglobulin
      G1; amino acid

<400> SEQUENCE: 30

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 31
<211> LENGTH: 54
<212> TYPE: DNA
<213> ORGANISM: Artificial Sequence
<220> FEATURE:
<223> OTHER INFORMATION: Anti-CD20 IFL-P2A-CD16V-BB-zeta, P2A; cDNA

<400> SEQUENCE: 31

gccacaaact ttagcctgct gaagcaggca ggcgacgtgg aggagaatcc agga           54


<210> SEQ ID NO 32
<211> LENGTH: 18
<212> TYPE: PRT
<213> ORGANISM: Artificial Sequence
<220> FEATURE:
<223> OTHER INFORMATION: Anti-CD20 IFL-P2A-CD16V-BB-zeta, P2A; amino
      acid

<400> SEQUENCE: 32

Ala Thr Asn Phe Ser Leu Leu Lys Gln Ala Gly Asp Val Glu Glu Asn
1               5                   10                  15

Pro Gly


<210> SEQ ID NO 33
<211> LENGTH: 63
<212> TYPE: DNA
<213> ORGANISM: Artificial Sequence
<220> FEATURE:
<223> OTHER INFORMATION: Anti-CD20 IFL-P2A-CD16V-BB-zeta, CD8alpha
      signal peptide; cDNA

<400> SEQUENCE: 33

cccgccctgc cagtgaccgc cctgctgctg cctctggccc tgctgctgca cgcagcccgc     60

cca                                                                   63


<210> SEQ ID NO 34
```

```
<211> LENGTH: 21
<212> TYPE: PRT
<213> ORGANISM: Artificial Sequence
<220> FEATURE:
<223> OTHER INFORMATION: Anti-CD20 IFL-P2A-CD16V-BB-zeta, CD8alpha
      signal peptide; amino acid

<400> SEQUENCE: 34

Pro Ala Leu Pro Val Thr Ala Leu Leu Leu Pro Leu Ala Leu Leu Leu
1               5                   10                  15

His Ala Ala Arg Pro
            20


<210> SEQ ID NO 35
<211> LENGTH: 576
<212> TYPE: DNA
<213> ORGANISM: Artificial Sequence
<220> FEATURE:
<223> OTHER INFORMATION: Anti-CD20 IFL-P2A-CD16V-BB-zeta, FCGR3A
      extracellular domain; cDNA

<400> SEQUENCE: 35

ggcatgcgga cagaggatct gcccaaggcc gtggtgtttc tggagcctca gtggtaccgc      60

gtgctggaga aggactccgt gaccctgaag tgtcagggcg cctattcccc tgaggataac     120

tctacacagt ggttccacaa tgagtctctg atctcctctc aggccagctc ctactttatc     180

gacgcagcaa ccgtggacga tagcggagag tatcggtgcc agacaaacct gtctaccctg     240

agcgatccag tgcagctgga ggtgcacatc ggatggctgc tgctgcaggc acctagatgg     300

gtgttcaagg aggaggatcc aatccacctg aggtgtcaca gctggaagaa taccgccctg     360

cacaaggtga catacctgca gaacggcaag ggccgcaagt acttccacca caattccgac     420

ttttatatcc caaaggccac cctgaaggat agcggctcct atttttgccg gggcctggtg     480

ggctccaaga acgtgtctag cgagacagtg aatatcacaa tcacccaggg cctggccgtg     540

tctacaatct cctctttctt tcctccaggc taccag                               576


<210> SEQ ID NO 36
<211> LENGTH: 192
<212> TYPE: PRT
<213> ORGANISM: Artificial Sequence
<220> FEATURE:
<223> OTHER INFORMATION: Anti-CD20 IFL-P2A-CD16V-BB-zeta, FCGR3A
      extracellular domain; amino acid

<400> SEQUENCE: 36

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
```

```
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190


<210> SEQ ID NO 37
<211> LENGTH: 207
<212> TYPE: DNA
<213> ORGANISM: Artificial Sequence
<220> FEATURE:
<223> OTHER INFORMATION: Anti-CD20 IFL-P2A-CD16V-BB-zeta, CD8alpha hinge
      and transmembrane; cDNA

<400> SEQUENCE: 37

accacaaccc ctgcaccaag accccctaca ccagcaccta ccatcgcaag ccagccactg      60

tccctgcggc ccgaggcctg taggccagca gcaggaggag cagtgcacac caggggcctg     120

gacttcgcct gcgatatcta tatctgggca cctctggcag gaacctgtgg cgtgctgctg     180

ctgagcctgg tcatcaccct gtactgc                                         207


<210> SEQ ID NO 38
<211> LENGTH: 69
<212> TYPE: PRT
<213> ORGANISM: Artificial Sequence
<220> FEATURE:
<223> OTHER INFORMATION: Anti-CD20 IFL-P2A-CD16V-BB-zeta, CD8alpha hinge
      and transmembrane; amino acid

<400> SEQUENCE: 38

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65


<210> SEQ ID NO 39
<211> LENGTH: 126
<212> TYPE: DNA
<213> ORGANISM: Artificial Sequence
<220> FEATURE:
<223> OTHER INFORMATION: Anti-CD20 IFL-P2A-CD16V-BB-zeta, CD137
      cytoplasmic domain; cDNA

<400> SEQUENCE: 39

aagagaggca ggaagaagct gctgtatatc ttcaagcagc cttttatgcg cccagtgcag      60

acaacccagg aggaggacgg ctgctcctgt cggttcccag aagaggagga gggaggatgt     120

gagctg                                                                126


<210> SEQ ID NO 40
<211> LENGTH: 42
```

<212> TYPE: PRT
<213> ORGANISM: Artificial Sequence
<220> FEATURE:
<223> OTHER INFORMATION: Anti-CD20 IFL-P2A-CD16V-BB-zeta, CD137 cytoplasmic domain; amino acid

<400> SEQUENCE: 40

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 41
<211> LENGTH: 339
<212> TYPE: DNA
<213> ORGANISM: Artificial Sequence
<220> FEATURE:
<223> OTHER INFORMATION: Anti-CD20 IFL-P2A-CD16V-BB-zeta, CD3zeta cytoplasmic domain; cDNA

<400> SEQUENCE: 41

```
agggtgaagt tttctcggag cgccgatgca ccagcatacc agcagggaca gaaccagctg     60

tataacgagc tgaatctggg ccggagagag gagtacgacg tgctggataa gaggcgcggc    120

agggaccccg agatgggagg caagccccgg agaaagaacc ctcaggaggg cctgtacaat    180

gagctgcaga aggacaagat ggccgaggcc tatagcgaga tcggcatgaa gggagagagg    240

cgccggggca agggacacga tggcctgtac cagggcctgt caacagcaac aaaagacact    300

tacgacgcac tgcacatgca ggctctgccc ccaagataa                           339
```

<210> SEQ ID NO 42
<211> LENGTH: 112
<212> TYPE: PRT
<213> ORGANISM: Artificial Sequence
<220> FEATURE:
<223> OTHER INFORMATION: Anti-CD20 IFL-P2A-CD16V-BB-zeta, CD3zeta cytoplasmic domain; amino acid

<400> SEQUENCE: 42

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 43
<211> LENGTH: 54
<212> TYPE: DNA
<213> ORGANISM: Artificial Sequence
<220> FEATURE:
<223> OTHER INFORMATION: P2A cDNA

<400> SEQUENCE: 43
gccacaaact ttagcctgct gaagcaggca ggcgacgtgg aggagaatcc agga 54

<210> SEQ ID NO 44
<211> LENGTH: 18
<212> TYPE: PRT
<213> ORGANISM: Artificial Sequence
<220> FEATURE:
<223> OTHER INFORMATION: P2A amino acid

<400> SEQUENCE: 44

Ala Thr Asn Phe Ser Leu Leu Lys Gln Ala Gly Asp Val Glu Glu Asn
1 5 10 15

Pro Gly

<210> SEQ ID NO 45
<211> LENGTH: 63
<212> TYPE: DNA
<213> ORGANISM: Artificial Sequence
<220> FEATURE:
<223> OTHER INFORMATION: T2A cDNA

<400> SEQUENCE: 45
ggaagcggag agggcagagg aagtctgcta acatgcggtg acgtcgagga gaatcctgga 60
cct 63

<210> SEQ ID NO 46
<211> LENGTH: 21
<212> TYPE: PRT
<213> ORGANISM: Artificial Sequence
<220> FEATURE:
<223> OTHER INFORMATION: T2A amino acid

<400> SEQUENCE: 46

Gly Ser Gly Glu Gly Arg Gly Ser Leu Leu Thr Cys Gly Asp Val Glu
1 5 10 15

Glu Asn Pro Gly Pro
20

<210> SEQ ID NO 47
<211> LENGTH: 69
<212> TYPE: DNA
<213> ORGANISM: Artificial Sequence
<220> FEATURE:
<223> OTHER INFORMATION: E2A cDNA

<400> SEQUENCE: 47
ggaagcggac agtgtactaa ttatgctctc ttgaaattgg ctggagatgt tgagagcaac 60
cctggacct 69

<210> SEQ ID NO 48
<211> LENGTH: 23
<212> TYPE: PRT
<213> ORGANISM: Artificial Sequence
<220> FEATURE:
<223> OTHER INFORMATION: E2A amino acid

<400> SEQUENCE: 48

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 49
<211> LENGTH: 75
<212> TYPE: DNA
<213> ORGANISM: Artificial Sequence
<220> FEATURE:
<223> OTHER INFORMATION: F2A cDNA

<400> SEQUENCE: 49
ggaagcggag tgaaacagac tttgaatttt gaccttctca agttggcggg agacgtggag 60
tccaaccctg gacct 75

<210> SEQ ID NO 50
<211> LENGTH: 25
<212> TYPE: PRT
<213> ORGANISM: Artificial Sequence
<220> FEATURE:
<223> OTHER INFORMATION: F2A amino acid

<400> SEQUENCE: 50

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 51
<211> LENGTH: 88
<212> TYPE: DNA
<213> ORGANISM: Artificial Sequence
<220> FEATURE:
<223> OTHER INFORMATION: Linker of FIG. 8C nucleotide

<400> SEQUENCE: 51
agctgctgct aaggcactgg aagcagaagc cgcggctaag gaggcggctg caaaagaagc 60
tgcagccaag gaagcagccg cgaaggca 88

<210> SEQ ID NO 52
<211> LENGTH: 46
<212> TYPE: PRT
<213> ORGANISM: Artificial Sequence
<220> FEATURE:
<223> OTHER INFORMATION: Linker of FIG. 8C amino acid

<400> SEQUENCE: 52

Ala Glu Ala Ala Ala Lys Glu Ala Ala Ala Lys Glu Ala Ala Ala Lys
1 5 10 15

Glu Ala Ala Ala Lys Ala Leu Glu Ala Glu Ala Ala Ala Lys Glu Ala
20 25 30

Ala Ala Lys Glu Ala Ala Ala Lys Glu Ala Ala Ala Lys Ala
35 40 45

<210> SEQ ID NO 53
<211> LENGTH: 342
<212> TYPE: DNA
<213> ORGANISM: Artificial Sequence
<220> FEATURE:
<223> OTHER INFORMATION: IL-15 of FIG. 8C nucleotide

<400> SEQUENCE: 53
aactgggtga atgtgatctc cgacctgaag aagatcgagg atctgatcca gtctatgcac 60
atcgacgcca ccctgtacac agagtccgat gtgcacccct cttgcaaggt gaccgccatg 120 aagtgtttc tgctggagct gcaggtcatc tccctggagt ctggcgacgc cagcatccac 180

-continued

```
gatacagtgg agaacctgat catcctggcc aacaattctc tgtcctctaa cggcaatgtg    240

accgagagcg gctgcaagga gtgtgaggag ctggaggaga agaatatcaa agagttcctg    300

cagagtttcg tccatatcgt ccagatgttt atcaatacct cc                       342


<210> SEQ ID NO 54
<211> LENGTH: 114
<212> TYPE: PRT
<213> ORGANISM: Artificial Sequence
<220> FEATURE:
<223> OTHER INFORMATION: IL-15 of FIG. 8C amino acid

<400> SEQUENCE: 54

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

FUNCTIONAL BINDERS SYNTHESIZED AND SECRETED BY IMMUNE CELLS

RELATED APPLICATION

This application is the U.S. National Stage of International Application No. PCT/IB2020/056659, filed Jul. 15, 2020, which designates the U.S., published in English, and claims the benefit of U.S. Provisional Application No. 62/875,455, filed on Jul. 17, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 44591154002_2_SEQUENCELISTING.txt; created Apr. 17, 2026; 35,668 Bytes in size.

BACKGROUND

Cancer immunotherapy broadly relates to directing immune responses to selectively attack tumor cells. The immunotherapeutic toolbox to treat cancer has been significantly enriched by the advent of chimeric antigen receptor (CAR)-directed T lymphocytes. The clinical experience with CAR-T cells demonstrates that T-lymphocytes, when adequately activated, can overcome resistance to chemotherapy, leading to major reduction in tumor burden, disease stabilization and, in some patients with B-cell leukemia and lymphoma, tumor eradication.[18-26] In CAR-T cells, T cell stimulation occurs via the expression of chimeric molecules with antibody-like properties.

Current CAR T-cell methodologies do not harness the full potential of the immune system to target cancer cells.

SUMMARY

Described herein is a peptide that includes a single-chain variable fragment (scFv) domain; a fragment crystallizable (Fc) domain; and a hinge domain joining the scFv and Fc domains. Also described are nucleic acids encoding the peptides described herein; vectors that include the nucleic acids, which encode the peptide described herein; immune cells (e.g., natural killer cells and T cells) that express the peptides described herein; and methods of making immune cells that express the peptides described herein.

The scFv domain can include an immunoglobulin variable light ($V_L$) domain, an immunoglobulin variable heavy ($V_H$) domain, and a linker domain joining the $V_L$ and $V_H$ domains. The linker domain can be $(G4S)_3$ (SEQ ID NO: 5).

The scFv domain can bind CD19, CD20, CD22, CD38, CD7, CD2, CD3, epidermal growth factor receptor (EGFR), CD123, CD33, B-cell maturation antigen (BCMA), mesothelin, human epidermal growth factor receptor 2 (Her2), prostate-specific membrane antigen (PSMA), disialoganglioside (GD2), PD-L1 (CD274), CD80 or CD86.

The Fc domain can include an immunoglobulin constant heavy 2 ($C_H2$) domain and an immunoglobulin constant heavy 3 ($C_H3$) domain. The Fc domain can be human IgG1 Fc domain.

The peptide can further include a signal peptide that is N-terminal to the scFv domain.

The peptide can further include a self-cleaving peptide joining the Fc domain to a chimeric receptor, wherein the chimeric receptor includes: a receptor domain; a hinge and transmembrane domain; a co-stimulatory signaling domain; and a cytoplasmic signaling domain.

The self-cleaving peptide can be a 2A peptide. The receptor domain can be CD16. The hinge and transmembrane domain can be a CD8a hinge and transmembrane domain. The co-stimulatory domain can be 4-1BB co-stimulatory domain. The cytoplasmic signaling domain can be a CD3ζ cytoplasmic signaling. The chimeric receptor can be CD16V-4-1BB-CD3ζ.

In one particular embodiment, the scFv domain binds CD19 or CD20; the Fc domain is a human IgG1 Fc domain; and the hinge domain is an IgG1 hinge domain; the vector further includes a CD8a signal peptide that is N-terminal to the scFv domain; and the vector further includes a chimeric receptor that is CD16V-4-1BB-CD3ζ.

The vector can be a murine stem cell virus (MSCV).

The peptide can further include IL-15 joined to the Fc domain by a linker. The linker that joins IL-15 to the Fc domain is selected from the group consisting of SEQ ID NO: 52 and $A(EAAAK)_zA$ (SEQ ID NO: 55), wherein z is an integer from 2 to 5.

Described herein is a peptide that includes a T-cell receptor (TCR) β domain; a first fragment crystallizable (Fc) domain joined to the TCR β domain; a TCR α domain; a self-cleaving peptide joining the Fc domain to the TCR α domain; and a second Fc domain joined to the TCR α domain. The peptide can further include a signal peptide joined to the T-cell receptor (TCR) β domain. The first Fc domain can be the same as the second Fc domain. The first Fc domain can be different from the second Fc domain. Also described are nucleic acids encoding the peptide and vectors that include the nucleic acid, which encodes the peptide.

Advantageously, the peptides described herein can be secreted by immune cells, such as T cells and NK cells. As a result, the immune cells can target and kill tumor cells without the need for exogenous administration of antibodies. NK cells can exert antibody-dependent cell cytotoxicity when the secreted peptides bind Fc receptors on the NK cell surface. T cells transduced with an Fc receptor can also exert antibody-dependent cell cytotoxicity. Moreover, the peptides can trigger phagocytosis of tumor cells by macrophages through interaction of Fc receptors on their cell surface. Finally, the peptides can kill tumor cells by inducing complement fixation.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A is a schematic representation of an IFL construct. A single-chain variable fragment (scFv) composed of variable domains of a light chain (VL) and a heavy chain (VH) is fused with a modified fragment crystallizable domain (Fc) composed of two of the three constant domains of heavy chain (CH2, CH3) of immunoglobulin G1 (IgG1) through a IgG1 hinge. FIG. 1B is flow cytometric dot plots that illustrate expression of GFP and IFL, detected by intracellular staining with an anti-human IgG Fc antibody, in NK cells transduced with GFP alone ("Control", left panel), anti-CD20 IFL gene ("aCD20 IFL", middle panel), or anti-CD19 IFL gene ("aCD19 IFL", right panel). Percentage of cells in each quadrant is shown. FIG. 1C is the same staining as in FIG. 1B in transduced T lymphocytes.

FIG. 2 is flow cytometric histograms show labelling of Jurkat (CD20−, CD19−), Ramos (CD20+, CD19+), and RS4;11 (CD20−, CD19+) cells after incubation incubated with culture supernatant obtained from either NK cells (top panel) or T cells (bottom panel), which had been transduced with GFP alone ("Control"), anti-CD20 IFL, or anti-CD19 IFL. IFLs bound to the surface of target cells were detected by a goat-anti human IgG antibody conjugated to phycoerythrin.

FIG. 3A is a plot showing levels of IFL secreted by NK cells or T cells form the same donor transduced with anti-CD20 IFL. Each symbol represents results from 1 of 3 donors tested. FIG. 3B is pie charts showing the percentage of fucosylated glycan (dark blue) and afucosylated glycan (light blue) of IFL secreted from transduced NK cells (left panel) or T cells (middle panel) according to N-glycan profiling by MALDI-TOF MS. Results with rituximab are shown for comparison.

FIG. 3C is bar diagrams illustrating percentage of relative intensity each various types of glycan in IFL secreted by transduced NK cells or T cells, or in rituximab. Schematic structures show various types of glycan.

FIG. 4A is charts showing results when Ramos (left panel) and SUDHL-4 cells (right panel) were incubated with 0.05 μg/mL of rituximab or IFLs from NK cells or T cells in the presence or absence of 5% complement. Cell killing was measured by counting viable cells by flow cytometry. FIG. 4B is plots showing results when IFL from NK cells or T cells (0.1 g/mL) were added to Ramos cells co-cultured with or without THP-1 cells for 48 hours. Cell killing was measured by counting viable target cells with Incucyte.

FIG. 5A is a graph of showing results when Raji cells were cultured with NK cells transduced with GFP alone ("NK-GFP") or anti-CD20 IFL ("NK-IFL") at a 1:1 E:T ratio. As a control, Ramos was cultured without NK cells ("no NK") or with NK-GFP in the presence of 1 ag/ml of rituximab. The number of viable Ramos cells was counted every 8 hours for 72 hours using Incucyte. FIG. 5B is a plot showing cytotoxicity of NK cells transduced with GFP alone or anti-CD19 IFL against RS4;11, OP-1 and Nalm-6. Shown are data for 4-hour assays at a E:T 2:1 ratio. Each symbol represents the results obtained with NK cells from 1 donor; bars correspond to the median value. FIG. 5C is a plot showing results when RS4;11 cells were incubated with medium alone or NK cells transduced with GFP alone or anti-CD20 or anti-CD19 IFLs at a E:T 2:1 ratio for 4 hours. Each symbol represents results obtained with NK cells from one donor.

FIG. 6A is a schematic representation of the gene construct containing IFL with CD16V-4-1BB-CD3ζ.

FIG. 6B is flow cytometric dot plots showing surface expression of CD16 in T cells transduced with GFP alone ("Control") or IFL-P2A-CD16-41BB-CD3ζ ("IFL+CD16R"). Percentage of cells in each quadrant is shown. FIG. 6C is flow cytometric dot plots showing expression of IFL after intracellular staining with anti-human Ig Fc antibody in the same cells. FIG. 6D is a graph of results when Ramos cells were co-cultured with or without T cells transduced with various constructs as indicated. The number of viable Ramos cells was counted every 8 hours for 72 hours by Incucyte.

FIG. 7A is a graph showing results when NOD-SCID-IL2RGnull mice were injected intravenously with $2\times10^7$ T cells transduced with anti-CD20 IFL-P2A-CD16-41BB-CD3ζ. Levels of IFL in plasma were measured by ELISA. FIG. 7B is a graph showing results when NOD-SCID-IL2RGnull mice (n=18) received one intraperitoneal (i.p.) injection of $2\times10^5$ Daudi labelled with luciferase. In 12 mice, we administered two i.p. injections of $2\times10^7$ T cells transduced with either anti-CD20 IFL-P2A-CD16V-4-1BB-CD3ζ (n=6) or GFP alone (n=6), 3 and 6 days after Daudi injection; 6 additional mice were injected with medium alone. Kaplan-Meier curves show the percentage of disease-free survival in the different groups.

FIG. 8A is a schematic of IFL with polymorphisms to increase the affinity for Fc receptor or complement. FIG. 8B is a schematic of IFL with polymorphisms to promote formation of hexamers. FIG. 8C is a schematic of IFL fusing with cytokine through a linker. FIG. 8D is a schematic of extracellular domain of TCR ac and R chains as binders for IFL. FIG. 8E is a schematic of IFL fusing with a ligand that binds a co-stimulatory molecule.

DETAILED DESCRIPTION

Figure 1A:
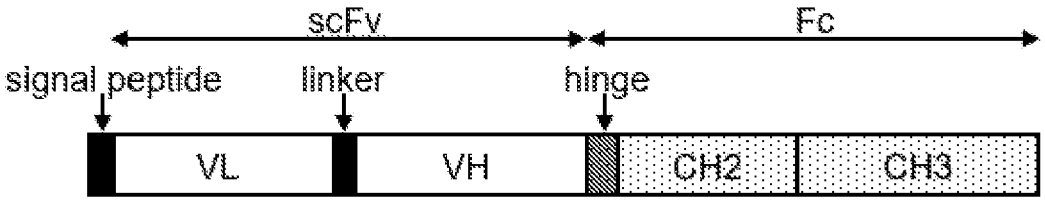
FIGS. 1A-C show design and expression of in vivo functional ligands (IFLs).

A description of example embodiments follows.

Monoclonal antibodies are integral to the contemporary treatment of cancer. Antibodies exert anti-tumor activity via several mechanisms including direct induction of cell death, complement activation, and engagement of immune cells. Antibodies bound to tumor cells can trigger antibody-dependent cell cytotoxicity (ADCC).[1-6] ADCC, which results from the engagement of Fc receptors (FcγR) expressed on the surface of natural killer (NK) cells,[7] is central to the clinical efficacy of antibodies; polymorphisms of the gene coding FcγRIIIa (FCRG3A or CD16) leading to receptors with higher affinity for Fc have been associated with better tumor responses in patients.[2,8-16] Other important mechanisms underlying the anti-tumor activity of antibodies include clearance of tumor cells by macrophages through antibody-dependent cell phagocytosis (ADCP), and complement-dependent cytotoxicity (CDC).[7,17]

The immunotherapeutic toolbox to treat cancer has been significantly enriched by the advent of chimeric antigen receptor (CAR)-directed T lymphocytes. The clinical experience with CAR-T cells demonstrates that T-lymphocytes, when adequately activated, can overcome resistance to chemotherapy, leading to major reduction in tumor burden, disease stabilization and, in some patients with B-cell leukemia and lymphoma, tumor eradication.[18-26] In CAR-T cells, T cell stimulation occurs via the expression of chimeric molecules with antibody-like properties.[27-31] Another approach leading to tumor-specific T cell activation is through the expression of high-affinity CD16 as a component of a chimeric receptor including both stimulatory and co-stimulatory signals.[32] Such receptor has the potential to significantly augment the anti-tumor effect of antibody therapy. Compared to CAR-T cells, it works in combination with other antibody-mediated mechanism, such as ADCP and CDC, resulting in a concerted anti-tumor effect. Moreover, by using multiple antibodies against weakly expressed antigens, vigorous T-cell responses can be elicited.

Described herein are methods that allow immune cells to produce binders with antibody-like function. These in vivo functional ligands (IFLs) are capable of triggering ADCC, ADCP and CDC, as well as cytokine stimulation. These can be expressed in NK cells and T cells, and in conjunction with CD16 chimeric receptors, to optimize effector functions.

While the particular examples described herein target CD20+ and CD19+ B-cells as a paradigm, the approach is applicable to targeting other antigens that are markers of cells in the pathogenesis of cancer and other diseases.

B-Cell Non-Hodgkin Lymphoma and CD20 and CD19

B-cell non-Hodgkin lymphoma (NHL) is a cancer of lymphoid blood cells. NHL inevitably progresses and is fatal if untreated. Standard treatment includes chemotherapy, antibody therapy, tyrosine kinase inhibitor therapy, and hematopoietic stem cell transplant. CD20 and CD19 are B-cell-specific antigens that are widely expressed in B-cell NHL (also referred to as B-NHL).

The vectors described herein can be used to generate modified T cells, which, in turn, can be used for targeted treatment of NHL. The processes described herein can be used to create transgenic T cells that can target CD20+ and CD19+ B-cells for destruction, thereby eradicating NHL and/or decreasing its severity.

Acute Lymphoblastic Leukemia and CD19

Acute lymphoblastic leukemia (ALL) is also a cancer of lymphoid blood cells. ALL progresses rapidly and is fatal if untreated. Standard treatment includes chemotherapy and hematopoietic stem cell transplant. CD19 is a B-cell-specific antigen that is expressed on all leukemic cells in the majority of cases of ALL.

The vectors described herein can be used to generate modified T cells, which, in turn, can be used for targeted treatment of ALL. The processes described herein can be used to create transgenic T cells that can target CD19+ B-cells for destruction, thereby eradicating ALL and/or decreasing its severity.

Nucleic Acids

As used herein, the term "nucleic acid" refers to a polymer comprising multiple nucleotide monomers (e.g., ribonucleotide monomers or deoxyribonucleotide monomers). "Nucleic acid" includes, for example, DNA (e.g., genomic DNA and cDNA), RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Natl. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., *J Mol Biol.* 215(3):403-10 (1990)).

In various embodiments, two nucleotide sequences, or two amino acid sequences, can have at least, e.g., 70%, 75%, 80%, 85%, 86%, 87%, 88%, 89%, 90%, 91%, 92%, 93%, 94%, 95%, 96%, 97%, 98%, 99%, or more, sequence identity. When ascertaining percent sequence identity to one or more sequences described herein, the sequences described herein are the reference sequences.

Vectors

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter. Gene delivery vectors generally include a transgene (e.g., nucleic acid encoding an enzyme) operably linked to a promoter and other nucleic acid elements required for expression of the transgene in the host cells into which the vector is introduced. Suitable promoters for gene expression and delivery constructs are known in the art. Recombinant plasmids can also comprise inducible, or regulatable, promoters for expression of an enzyme in cells.

Various gene delivery vehicles are known in the art and include both viral and non-viral (e.g., naked DNA, plasmid) vectors. Viral vectors suitable for gene delivery are known to those skilled in the art. Such viral vectors include, e.g., vector derived from the herpes virus, baculovirus vector, lentiviral vector, retroviral vector, adenoviral vector, adeno-associated viral vector (AAV), and murine stem cell virus (MSCV). The viral vector can be replicating or non-replicating. Such vectors may be introduced into many appropriate host cells, using methods disclosed or cited herein or otherwise known to those skilled in the relevant art.

Non-viral vectors for gene delivery include naked DNA, plasmids, transposons, and mRNA, among others. Non-limiting examples include pKK plasmids (Clonetech), pUC plasmids, pET plasmids (Novagen, Inc., Madison, Wis.), pRSET or pREP plasmids (Invitrogen, San Diego, Calif.), pMAL plasmids (New England Biolabs, Beverly, Mass.). Such vectors may be introduced into many appropriate host cells, using methods disclosed or cited herein or otherwise known to those skilled in the relevant art.

In certain embodiments, the vector comprises an internal ribosome entry site (IRES). In some embodiments, the vector includes a selection marker, such as an ampicillin resistance gene (Amp). In some embodiments, the nucleic acid encodes a fluorescent protein, such as green fluorescent protein (GFP) or mCherry. In some embodiments, the nucleic acid is suitable for subcloning into pMSCV-IRES-GFP between EcoRI and XhoI. In some embodiments, the vector contains a multiple cloning site (MCS) for the insertion of the desired gene.

Although the genetic code is degenerate in that most amino acids are represented by multiple codons (called "synonyms" or "synonymous" codons), it is understood in the art that codon usage by particular organisms is nonrandom and biased towards particular codon triplets. Accordingly, in some embodiments, the vector includes a nucleotide sequence that has been optimized for expression in a particular type of host cell (e.g., through codon optimization). Codon optimization refers to a process in which a polynucleotide encoding a protein of interest is modified to replace particular codons in that polynucleotide with codons that encode the same amino acid(s), but are more commonly used/recognized in the host cell in which the nucleic acid is being expressed. In some aspects, the polynucleotides described herein are codon optimized for expression in T cells.

In Vivo Functional Ligands

FIG. 1A is a schematic representation of an in vivo functional ligand (IFL) construct. The IFL includes a single chain variable fragment (scFv) domain, a modified fragment crystallizable (Fc) domain, and a hinge domain joining the scFv and the modified Fc domains. Preferably, an N-terminal signal peptide (leader peptide) is included that targets the IFL towards the secretory pathway and, ultimately, secretion by the cell. Signal peptides of surface proteins are generally suitable, and an example is a CD8a signal peptide.

The scFv domain typically includes an immunoglobulin variable light ($V_L$) domain, an immunoglobulin variable heavy ($V_H$) domain, and a linker domain joining the $V_L$ and $V_H$ domains. The relative positions of the $V_L$ and $V_H$ domains can be reversed, but they are both N' to the modified Fc domain, as illustrated in FIG. 1A.

The scFv domain targets an antigen of interest, such as an antigen of a tumor cell. One particular scFv described herein is an anti-CD19 single-chain variable fragment (anti-CD19 scFv). Another particular scFv described herein is an anti-CD20 single-chain variable fragment (anti-CD20 scFv).

While the embodiments described herein pertain to anti-CD19 construct and an anti-CD20 construct, a similar approach can be applied to generate constructs for other target antigens, such as CD22, CD123, CD33, B-cell maturation antigen (BCMA), mesothelin, human epidermal growth factor receptor 2 (Her2), prostate-specific membrane antigen (PSMA), disialoganglioside (GD)-2, PD-L1 (CD274), CD80 or CD86. For example, based on the schema in FIG. 5A, the anti-CD19 scFv portion can be replaced with a different scFv that specifically binds to a different target antigen. Other targets are suitable, including CD22, CD123, CD33, B-cell maturation antigen (BCMA), mesothelin, human epidermal growth factor receptor 2 (Her2), prostate-specific membrane antigen (PSMA), disialoganglioside (GD2), PD-L1 (CD274), CD80 or CD86.

A hinge domain joins the scFv and modified Fc domains, though in some instances the hinge domain may be considered part of the Fc domain. An example of a hinge domain is the IgG hinge domain. The construct can also include an N-terminal signal peptide, such as a CD8a signal peptide (see SEQ ID NOS: 21 and 22).

A variety of linker domains between $V_L$ and $V_H$ domains are suitable. In some embodiments, the linker domain can be $(G4S)_3$ (SEQ ID NO: 5). In other embodiments, the linker domain can be $(EAAAK)_3$ (SEQ ID NO: 56). $(G4S)_3$ is an example of a flexible linker, while $(EAAAK)_3$ (SEQ ID NO: 56) is an example of a more rigid linker.

A variety of hinge domains are suitable. In some embodiments, the hinge domain can be a IgG hinge domain. In some embodiments, the hinge can be a plurality of amino acid residues. In some embodiments, the hinge domain can be a hinge domain from IgE, IgA, IgD, or CD8a.

Figure 6A:
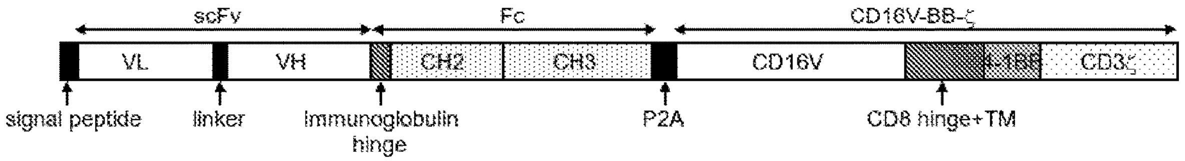
FIGS. 6A-D show ADCC mediated by immune cell-derived IFL.

In some embodiment, the construct is a bicistronic vector that also encodes a chimeric receptor, as illustrated in FIG. 6A. The chimeric receptor can include a receptor domain, a hinge and transmembrane domain, a co-stimulatory signaling domain, and a cytoplasmic signaling domain. In the construct of FIG. 6A, the chimeric receptor is joined with the modified Fc domain by a 2A peptide, which is a self-cleaving peptide. By joining the chimeric receptor with the scFv and Fc domains, coexpression of both proteins can be expressed from a single vector. Examples of 2A peptides are P2A (SEQ ID NOS: 43 and 44), T2A (SEQ ID NOS: 45 and 46), E2A (SEQ ID NOS: 47 and 48), and F2A (SEQ ID NOS: 49 and 50), though other 2A peptides are known in the art.

Modifications to IFL Design

The design of the IFL construct tested in this study can be further modified to enhance some its functions and/or widen the range of its specificities. For example, the modified Fc can be further altered to increase its affinity for Fc receptors in NK cells and macrophages, thus enhancing ADCC and ADCP, and/or to increase its capacity to fix complement.[41-43]

Figure 8A:
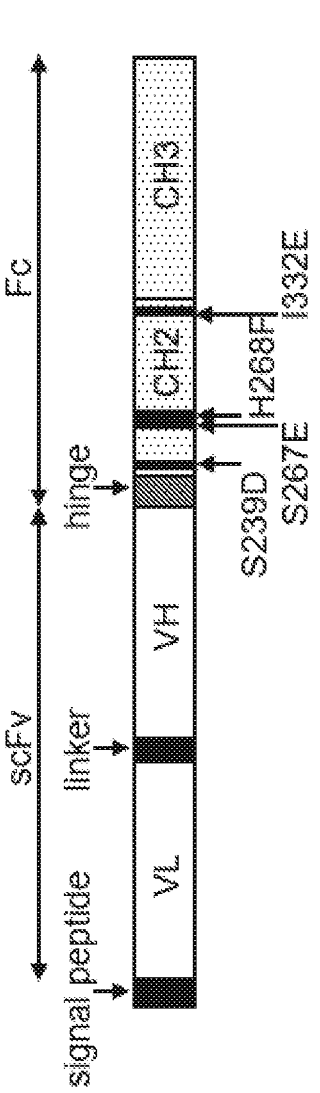
FIGS. 8A-E are examples of IFL variants.

In one modification (FIG. 8A), examples of two mutations introduced in the $C_H2$ domain of the Fc (serine in place of aspartic acid in position 239, S239D; and isoleucine in place of glutamic acid in position 332, 1332E) are made to improve affinity for Fc receptors; two other mutations (S267E and H268F) are made to increase complement fixation.[41,43]

Figure 8B:
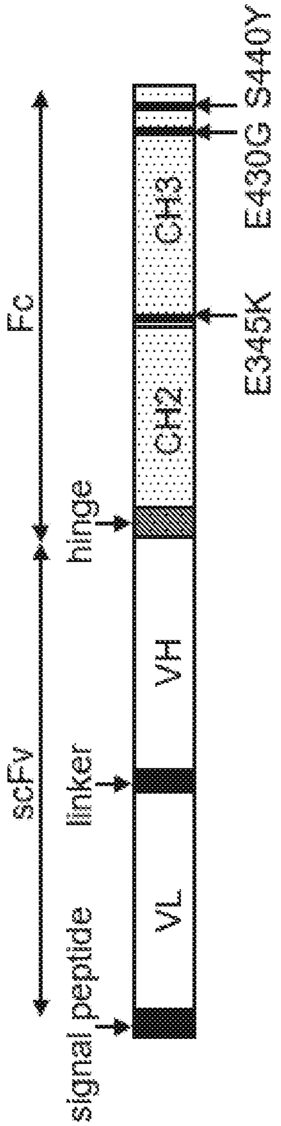

In another modification (FIG. 8B), examples of mutations introduced in the $C_H2$ domain of the Fc (E345K, E430G and S440Y) are made to promote hexamer formation. IFL hexamer could increase ADCC and CDC.[44,48]

Figure 8C:
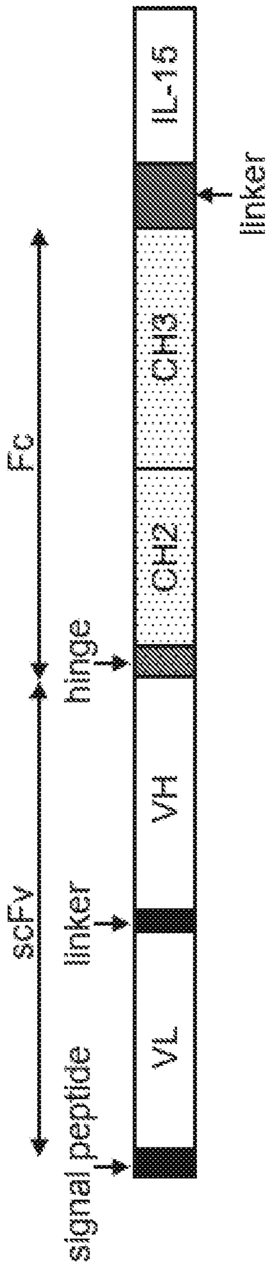

In another modification (FIG. 8C), IL-15 is added to the IFL construct; this cytokine promotes activation and expansion of immune cells.[45,46] The IFL and IL-15 are joined by a linker. A variety of linker domains between the IFL construct and cytokine are suitable. In some embodiments, the linker domain is the amino acid of SEQ ID NO: 52, produced by its corresponding nucleotide sequence (SEQ ID NO: 51). In other embodiments, the linker domain can be $A(EAAAK)_zA$ (SEQ ID NO: 55), wherein z is an integer from 2 to 5.

In another modification (FIG. 8E), ligands that bind co-stimulatory molecules of immune cells such as 4-1BB (CD137), CD28, or OX40 (CD134), are added to the IFL construct. The IFL and the co-stimulatory ligand are joined by a linker. A variety of linker domains between the IFL construct and co-stimulatory ligand are suitable, and are generally the same linker domains that are suitable for between the IFL construct and cytokine of FIG. 8C.

Figure 8D:
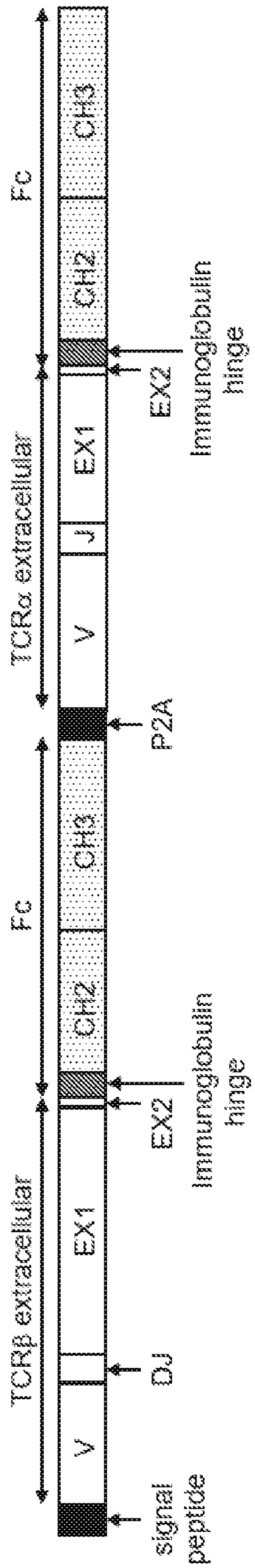
Figure 8E:
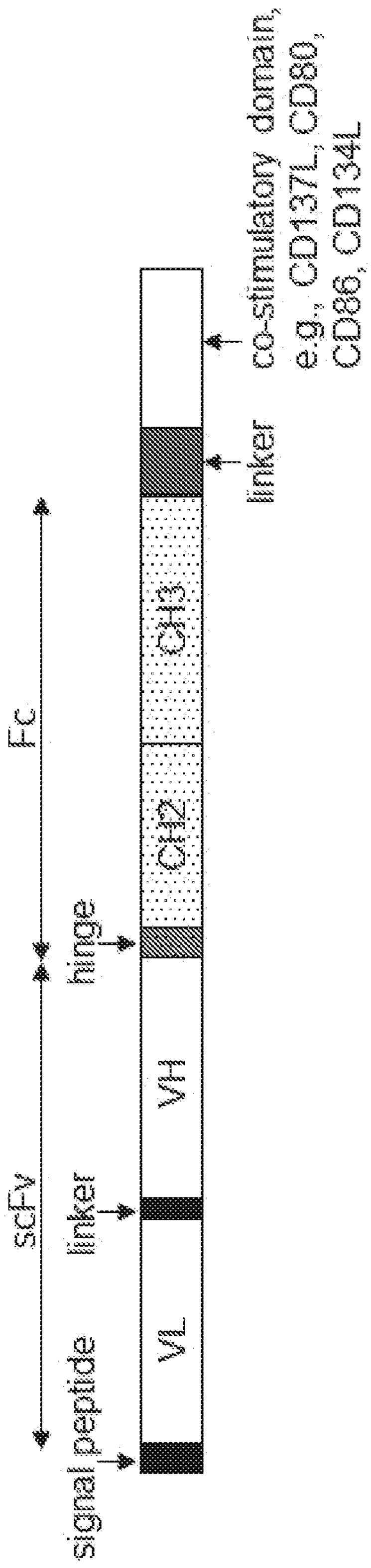

FIG. 8D shows a construct in which the binding domain of the IFL is the extracellular domain of a T-cell receptor (TCR) directed against Epstein-Barr virus.[47] Such IFLs can recognize peptides produced by virally-infected or oncogenically transformed cells and can be expressed on the cell membrane in the context of MHC/HLA molecules. Therefore, such IFLs could be used to target viral peptides or peptides produced by cancer cells that cannot be recognized by antibodies or scFv derived from antibodies.

Methods of Making Transgenic Host Cells

Described herein are methods of making a transgenic host cell, such as transgenic natural killer (NK) cells or transgenic T cells. The transgenic host cells can be made, for example, by introducing one or more of the vector embodiments described herein into the host cell.

In one embodiment, the method comprises introducing into a host cell a vector that includes a nucleic acid that encodes an IFL. In some embodiments, a nucleic acid, such as a bicistronic vector, expresses the IFL along with a chimeric receptor. In some embodiments, two separate vectors can be used to create a transgenic cell, such as a transgenic T cell, that expresses an IFL and a chimeric receptor.

In some embodiments, one or more of the nucleic acids are integrated into the genome of the host cell. In some embodiments, the nucleic acids to be integrated into a host genome can be introduced into the host cell using any of a variety of suitable methodologies known in the art, including, for example, homologous recombination, CRISPR-based systems (e.g., CRISPR/Cas9; CRISPR/Cpf1) and TALEN systems.

Host Cells

A variety of host cells are suitable for use in making transgenic host cells. Most commonly, the host cells are immune cells, such as natural killer (NK) cells or T lymphocyte cells.

As used herein, "natural killer cells" ("NK cells") refer to a type of cytotoxic lymphocyte of the immune system. NK cells provide rapid responses to virally infected cells and respond to transformed cells. Typically, immune cells detect peptides from pathogens presented by major histocompatibility complex (MHC) molecules on the surface of infected cells, triggering cytokine release, causing lysis or apoptosis. NK cells are unique, however, as they have the ability to recognize stressed cells regardless of whether peptides from pathogens are present on MHC molecules. They were named "natural killers" because of the initial notion that they do not require prior activation in order to kill target. NK cells are large granular lymphocytes (LGL) and are known to differentiate and mature in the bone marrow from where they then enter into the circulation. NK cell can also kill tumor cells if antigens on the surface of tumor cells are bound by antibodies; the Fc portion of the antibody bind Fc receptors (CD16) on the surface of NK cells and triggers cytotoxicity, a process known as antibody-dependent cell cytotoxicity (ADCC).

As used herein, "T lymphocytes" or "T cells" refers to lymphocytes that mature in the thymus. T cells can be further characterized into subpopulations, including T helper (TH) cells, T cytotoxic (Tc) cells, and T regulatory ($T_{reg}$) cells. TH and Tc cells can be characterized according to the presence or absence of membrane glycoproteins CD4 and CD8. Generally, TH cells express CD4 on their surface, while Tc cells express CD8 on their surface. T helper cells can be further characterized as TH1 cells and TH2 cells. T cells can also exert ADCC if transduced with a receptor encoding CD16 and signaling molecules.[32]

In some aspects, the NK cell or the T cells are mammalian cells. Examples of "mammalian" or "mammals" include primates (e.g., human), canines, felines, rodents, porcine, ruminants, and the like. Specific examples include humans, dogs, cats, horses, cows, sheep, goats, rabbits, guinea pigs, rats and mice. In a particular aspect, the mammalian T or NK cell is a human T or NK cell.

Upon introducing into a host cell, a vector that includes a nucleic acid that encodes an IFL, the host cell becomes a transgenic host cell that expresses the IFL. Typically, the IFL is secreted by the transgenic host cell.

Values and Ranges

Unless otherwise indicated or otherwise evident from the context and understanding of one of ordinary skill in the art, values that are expressed as ranges can assume any specific value or subrange within the stated ranges in various embodiments, unless the context clearly dictates otherwise. "About" in reference to a numerical value generally refers to a range of values that fall within ±8%, in some embodiments ±6%, in some embodiments ±4%, in some embodiments ±2%, in some embodiments ±1%, in some embodiments ±0.5% of the value unless otherwise stated or otherwise evident from the context.

EXEMPLIFICATION

Materials and Methods

Cells

Human cell lines RS4;11 and Nalm-6 (B-cell leukemia), Ramos, Raji and Daudi (B-cell lymphoma) and Jurkat (T-cell leukemia) were obtained from the American Type Culture Collection (Rockville, MD). The B-cell leukemia cell line OP-1 was established at our laboratory.[33] We transduced Nalm-6 and Daudi with a murine stem cell virus (MSCV)-internal ribosome entry site (IRES)-green fluorescent protein (GFP) retroviral vector (from the Vector Development and Production Shared Resource of St. Jude Children's Research Hospital, Memphis, TN) containing firefly luciferase gene. We also transduced Ramos and Raji with the MSCV retroviral vector containing mCherry gene. Transduced cells were selected for their GFP or mCherry expression, respectively, using a MoFlo cell sorter (Beckman Coulter, Brea, CA). To have Nalm-6 express CD20 on the surface, we subcloned human CD20 gene in cytomegalovirus plasmid (pCMV6) vector (Origene, Rockville, MD) into MSCV-IRES-GFP vector and transduced Nalm-6 with the CD20 gene. Nalm-6 cells expressing CD20 were selected using MoFlo sorter after staining with anti-CD20 antibody (BD Biosciences, San Jose, CA). Cell lines were cultured in RPMI-1640 (ThermoFisher Scientific, Waltham, MA) with 10% fetal bovine serum (FBS, Thermo Fisher Scientific) and 1% penicillin-streptomycin.

Peripheral blood was obtained from discarded products of platelet donations from healthy donors at the National University Hospital Blood Bank, Singapore. Mononucleated cells were isolated by a density gradient centrifugation with Lymphoprep (Axis-Shield, Oslo, Norway) and washed twice in RPMI-1640. For viral transduction, NK cells were expanded from the isolated mononucleated cells with the genetically modified K562-mb15-41BBL, previously established in our laboratory.[34,35] T cells were activated by T cell TransAct (Miltenyi Biotec, Bergisch Gladbach, Germany) and cultured in TexMACS medium (Miltenyi Biotec) with interleukin-2 (IL-2, Proleukin, Novartis, Basel, Switzerland, 100 IU/mL).

Plasmids and Viral Transduction

We designed IFLs composed of single-chain variable fragment (scFv) linking with a modified fragment crystallizable domain (Fc) of human immunoglobulin G1 (IgG1). The amino acid sequence of the signal peptide, scFv against CD20 and modified Fc of IgG1 was obtained from the sequence of rituximab described in DrugBank (drugbank.ca; Accession No. DB00073). The scFv sequence against CD19 was from anti-CD19-41BB-CD3ζ CAR previously developed in our laboratory.[31] The variable domains of heavy and light chain were connected by a flexible linker sequence encoding $(Gly4Ser)_3$ (SEQ ID NO: 5). The linked scFv was joined to the signal peptide and the hinge followed by constant heavy domains 2 and 3 ($C_H2$, $C_H3$) of IgG1. The anti-CD20 IFL was fused with CD16V-4-1BB-CD3, which could have T cells exert ADCC as previously described by our laboratory, through a self-cleaving 2A peptide (P2A).[36] The gene was subcloned into the MSCV vector with or without GFP.

Gene transduction by retroviral vector was performed as previously described.[37] Briefly, MSCV retroviral vector was added to RetroNectin-coated (Takara, Otsu, Japan) tubes and incubated at 4° C. for 16 hours. Then, activated NK cells or T lymphocytes were added to the tubes after removal of the supernatant and incubated at 37° C. in 5% $CO_2$ for 24 hours. The transduction procedure was repeated one more time on the following day. Transduced cells were maintained in RPMI-1640, 10% FBS with IL-2.

Determination of IFL Expression and Specificity

To detect the IFL expression, transduced cells were stained with phycoerythrin (PE)-conjugated anti-human IgG antibody (SouthernBiotech, West Grove, PA) after permeabilizing by 8E reagent (a permeabilization reagent developed in our laboratory). CD16 and CD3 expression on the cell surface were determined by anti-CD16-PE (clone B73.1, BD Biosciences) and anti-CD3-APC (clone SK7, BD Biosciences), respectively.

For the specificity of IFLs, culture supernatant from transduced cells was added to Jurkat (CD20 negative, CD19 negative), Ramos (CD20 positive, CD19 positive), or RS4;11 (CD20 negative, CD19 positive) at 1 μg/mL and incubated for 10 minutes. The IFLs bound on the cell surface were detected with PE-conjugated anti-human IgG antibody. Cell staining was analyzed using BD LSRFortessa (BD Biosciences).

Measurement of IFL Concentration and Glycosylation Analysis

The IFL concentration in culture supernatant from transduced cells was measured by enzyme-linked immunosorbent assay (ELISA). Briefly, culture supernatant containing IFL or rituximab was incubated on plates coated with PE-conjugated anti-human IgG antibody for one hour and washed. Subsequently, horseradish peroxidase (HRP)-conjugated anti-Rituximab antibody (MB2A4, Bio-Rad, Hercules, CA) was added to the plates and incubated for one hour. Fluorescence was measured by Infinite 200 PRO (Tecan, Mannedorf, Switzerland) after adding QuantaBlu Fluorogenic Peroxidase Substrate (Thermo Fisher). The IFL concentration was determined by the standard curve prepared with rituximab.

Glycosylation analysis was performed by Proteodynamics (Riom, France). Briefly, IFLs in culture supernatant of transduced cells were concentrated by a dialysis membrane (Amicon Ultra-15 Centrifugal Filter Units, Merck Millipore, Burlington, MA) and purified using NAB Protein G Spin kit (Thermo Fisher). The purified IFLs were denatured in 0.5% sodium dodecyl sulfate (SDS) and 1% β-mercaptoethanol and deglycosylated by PNGase F (Promega, Fitchburg, WI). The PNGase released N-glycans were purified on Hypercarb Hypersep 200 mg (Thermo Fisher) and permethylated by sodium hydroxide, dimethyl sulfoxide (DMSO) and methyl iodide (ICH3), before MALDI-TOF MS analysis using an Autoflex speed mass spectrometer (Bruker, Billerica, MA).

Cytotoxicity Assays In Vitro

For CDC assay, Ramos or SUDHL-4 in RPMI/10% FBS medium with or without 5% complement (Sigma-Aldrich, Saint Louis, MO) were plated, and Rituximab or anti-CD20 IFL was added at 0.05 μg/ml. Viable cells were counted by Accuri CD6 (BD Biosciences) after incubation at 37° C. in 5% $CO_2$ for 2 hours.

To test ADCP, Ramos cells labelled with mCherry were cultured with or without THP-1 at a 1:1 ratio for 48 hours in the presence of anti-CD20 IFL or rituximab at 0.1 μg/ml. Ramos cells were counted by IncuCyte Zoom System (Essen BioScience, Ann Arbor, MI).

For ADCC assay, target cells stained with calcein AM (Thermo Fisher) were co-cultured with transduced NK cells or T lymphocytes at a 2:1 effector-to-target (E:T) ratio for 4 hours. Viable target cells were counted by flow cytometry. In other tests, target cells expressing mCherry were incubated with NK cells or T lymphocytes with IL-2 (200 IU/mL for NK cells, 100 IU/mL for T cells) at 37° C. in 5% $CO_2$. As a control, rituximab was added to NK cells with GFP alone at 1.0 μg/ml. The target cells were counted using IncuCyte Zoom System every 8 hours for 3 days.

IFL Kinetics and Dynamics in Mouse Model

To measure plasma concentration of IFL secreted from T cells, NOD.Cg-Prkd$^{scid}$ IL2rg$^{tm1Wjl}$/SzJ (NOD/scid IL2RGnull) mice (The Jackson Laboratory, Bar Harbor, ME) we injected intravenously (i.v.) $2\times10^7$ T cells transduced with anti-CD20 IFL-P2A-CD16V-4-1BB-CD3ζ, followed by $2\times10^5$ Nalm-6 expressing CD20 two days later. Mice also received 20,000 IU of IL-2 intraperitoneally every 2 days for three weeks. IFL in plasma was measured by ELISA.

To examine antitumor activity in vivo, luciferase-labelled Daudi was injected in NOD/scid IL2RGnull mice at $2\times10^5$ cells per mouse intraperitoneally (i.p.). Three and 6 days later, mice received T cells transduced with anti-CD20 IFL-P2A-CD16V-4-1BB-CD3ζ at $2\times10^7$ cells per mouse i.p. Other mice received $2\times10^7$ T cells transduced with GFP or 0.2 ml of RPMI 1640 only, instead of T cells. All mice received 20,000 IU of IL-2 every 2 days for one or three weeks. Growth of Daudi cells was measured using the Xenogen IVIS-200 System (Caliper Life Sciences, Waltham, MA) after injection of D-luciferin potassium salt (Perkin Elmer, Waltham, MA). Luminescence was analyzed with the Living Image 3.0 software (Perkin Elmer). Mice were euthanized when luminescence reached $1\times10^{11}$ photons per second or physical signs warranting euthanasia appeared.

Results

Design and Expression of IFLs

Figure 1B:
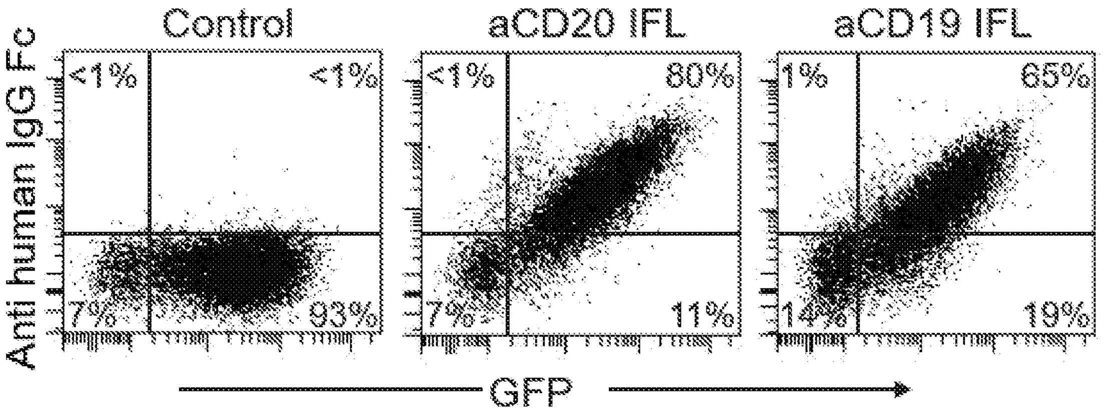
Figure 1C:
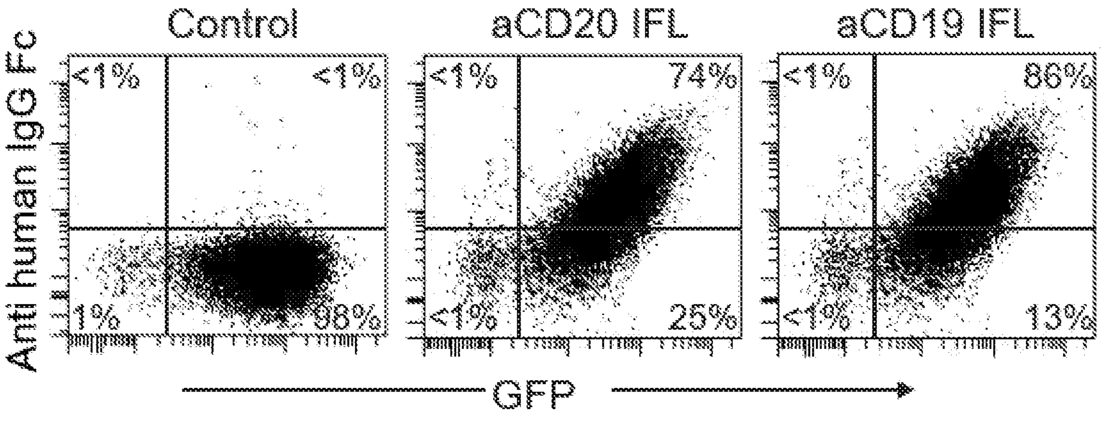

We first generated a scFv fragment from the public sequence of the anti-CD20 antibody rituximab. This scFv, as well as an anti-CD19 scFv previously developed in our laboratory,[31] were linked to the hinge and heavy chain constant domain 2 ($C_H2$) and 3 ($C_H3$) of human IgG1 (FIG. 1A). We inserted the IFL genes into an MSCV retroviral vector also containing the GFP gene, and transduced them in expanded NK cells. To determine whether IFLs were synthesized by the transduced cells, we performed intracellular staining targeting the Fc component. As shown in FIG. 1B, most NK GFP+ cells also expressed either the anti-CD20 or the anti-CD19 IFL. Similar results were seen when peripheral blood T lymphocytes were transduced with the same construct (FIG. 1C).

Figure 2:
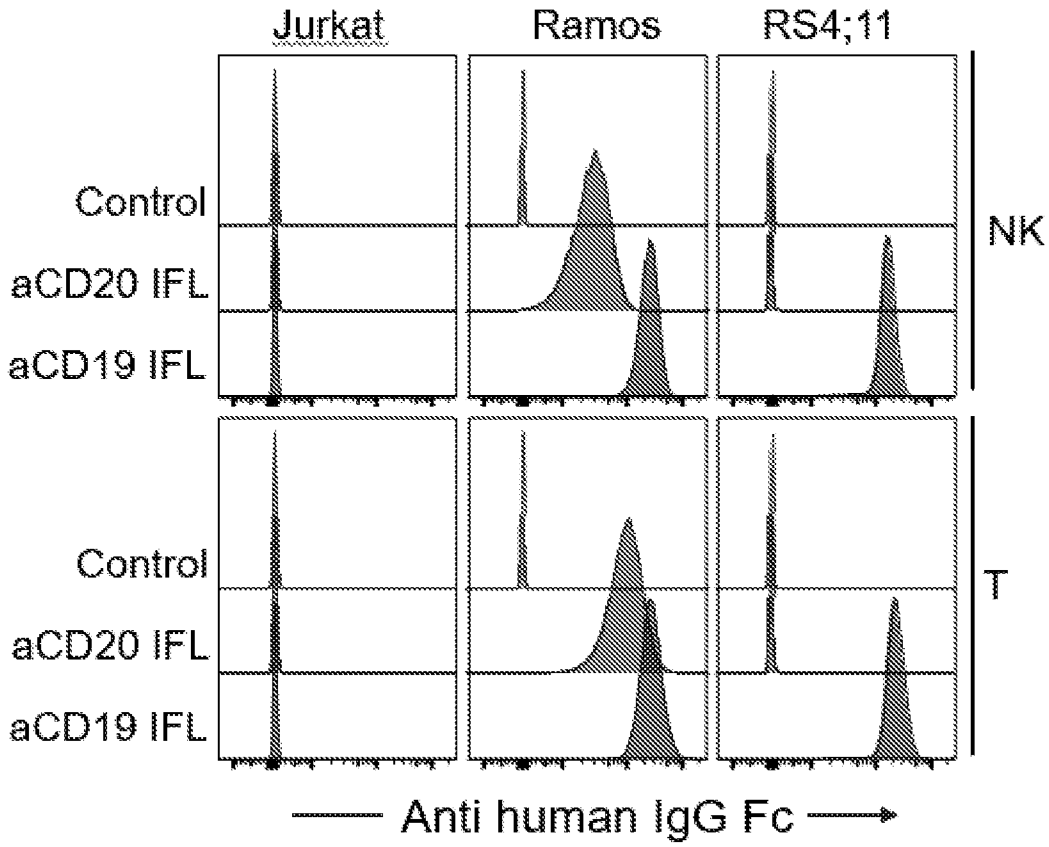
FIG. 2 shows that IFLs are specific for their cognate binder.

We determined whether the IFLs could bind their cognate target. As shown in FIG. 2, the secreted anti-CD19 IFL labelled CD19+ cells Ramos and RS4;11, while the anti-CD20 IFL, labelled only the CD20+ Ramos cell line but not the CD20− RS4;11 cell line. Neither labelled the CD19−CD20− T cell line Jurkat (FIG. 2).

IFL Characterization

Figure 3A:
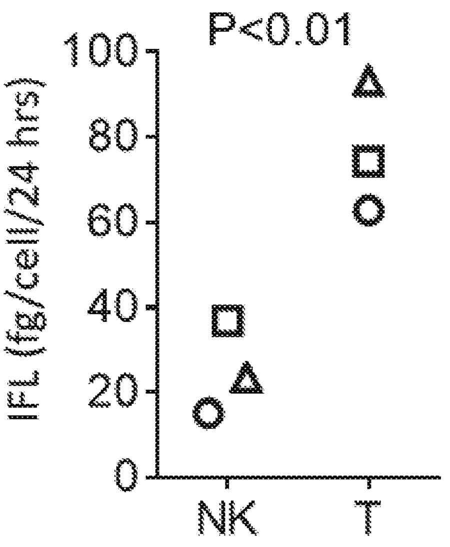
FIGS. 3A-C show synthesis and glycosylation of IFL.

To measure the capacity of immune cells to produce IFLs, we collected the culture media from anti-CD20 IFL transduced cells and measured the concentration of antibody by ELISA, using an anti-idiotypic rituximab antibody. As shown in FIG. 3A, both NK and T cells secreted the anti-CD20 IFL. Notably, the amount of IFL measured in the T cells' supernatant was significantly higher than that measured in the NK cells' supernatant ($P<0.01$). The amount of IFL secreted from $1\times10^6$ transduced NK cells for 24 hours was equivalent to 23.5 ng of rituximab (range, 15.1-36.8 ng, n=3). That secreted by T cells was equivalent to 74.3 ng (range, 62.8-93.2 ng, n=3).

Figure 3B:
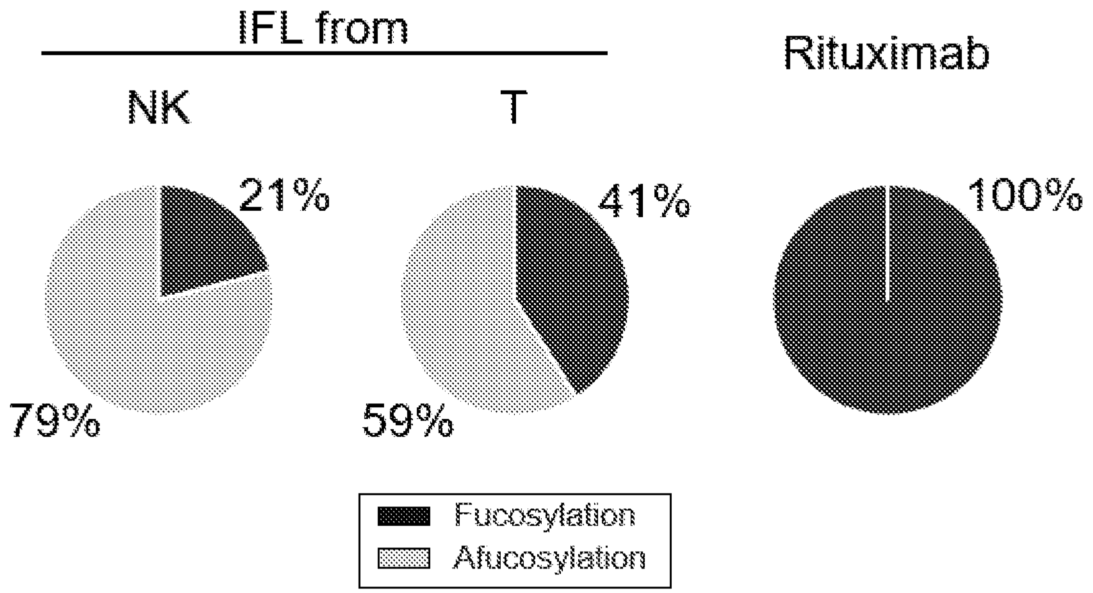
Figure 3C:
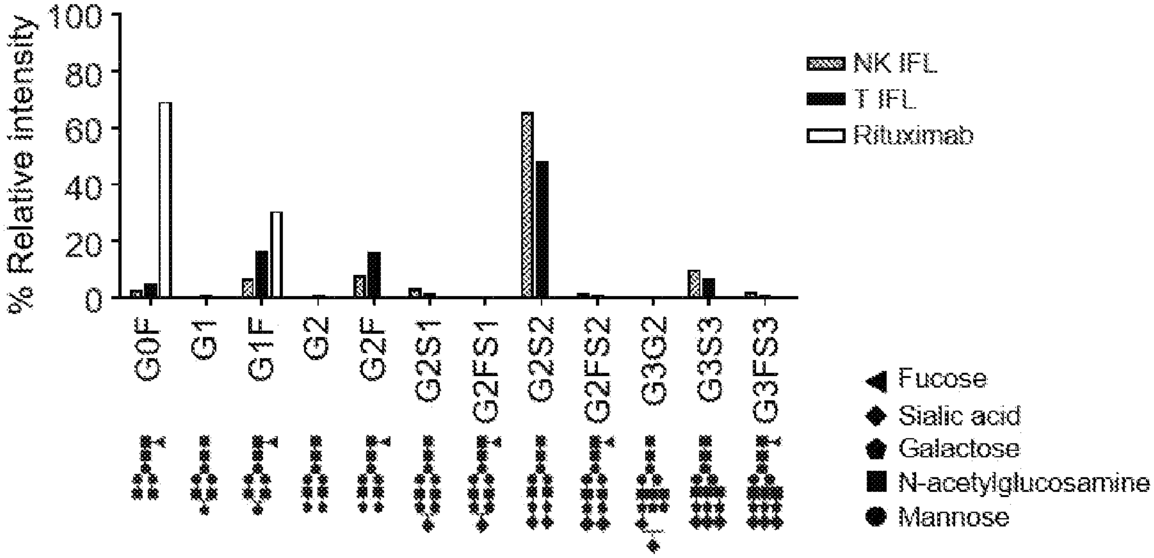

To define the type of post-translational modification profile of the constructs produced by immune cells, we performed an analysis of the N-linked glycans bound to the modified Fc domain using MALDI-TOF. Twelve N-glycan structures were detected for the NK cell IFL, and 8 for the T cell IFL. For both, the dominant structure was a di-sialylated bi-antennary N-glycan ([M+Na]+2792) without core-fucose, containing 2 galactose and 2 terminal sialic acid named G2S2. Interestingly, 79% and 59% of Fc glycans were afucosylated when IFL were produced by NK and T cells, respectively. (FIG. 3B, C). As a control, we also tested the N-linked glycan pattern of Rituximab; the detected N-glycans were two fucosylated bi-antennary N-glycans ([M+Na]+1836=GOF, 2040=G1F).

IFLs Mediate CDC, ADCP and ADCC

Figure 4A:
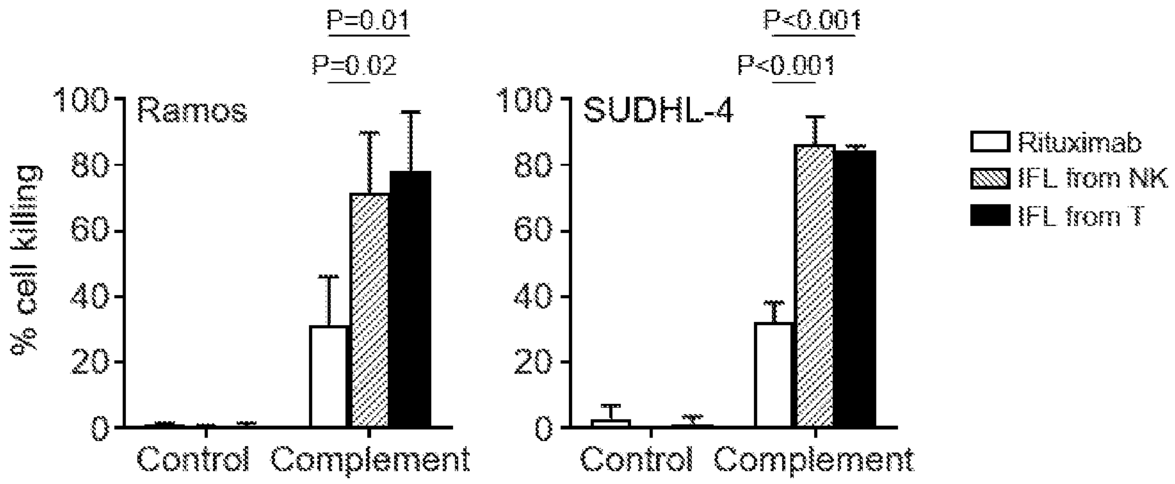
FIGS. 4A-B show CDC and ADCP mediated by immune cell-derived IFL.

To test whether IFLs could mediate CDC, we incubated the CD20+ B-lymphoma cell lines Ramos, SUDHL-4 and Raji with different concentrations of anti-CD20 IFL (collected from supernatants of NK cells or T cells transduced with IFL) and 5% complement for 2 hours. In parallel tests, the anti-CD20 IFL was replaced by rituximab. As shown in FIG. 4A, IFL triggered massive lysis of both Ramos and SUDHL-4 cell lines (known to be susceptible to complement lysis), while the complement-resistant Raji cells remained largely unaffected.[38,39]

Figure 4B:
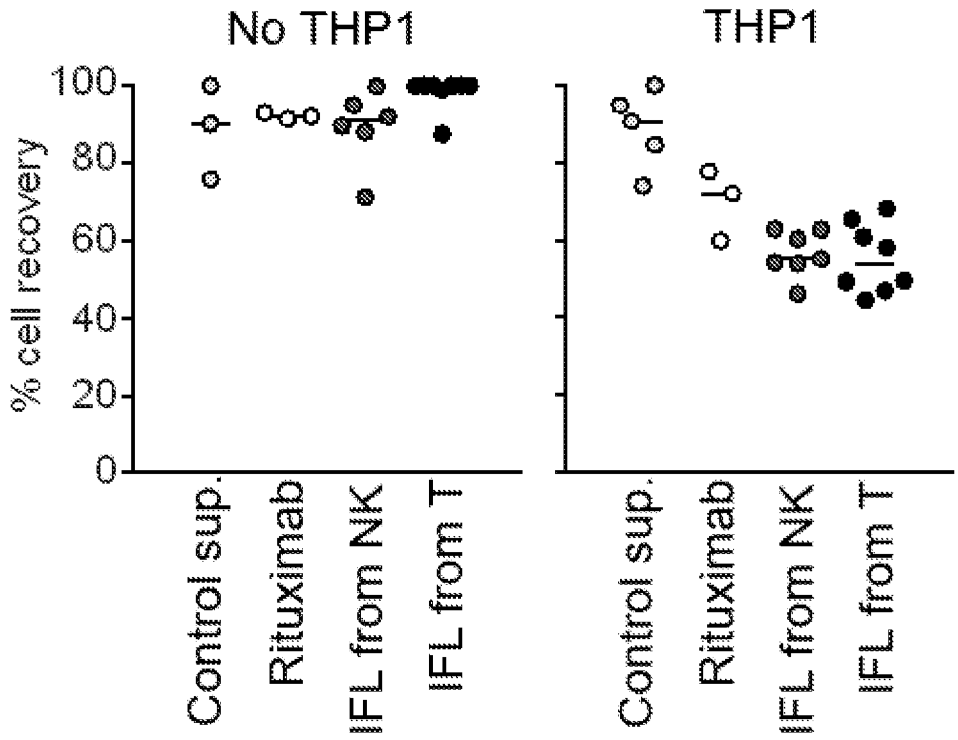

ADCP was tested by co-culturing Ramos with the monocytic cell line, THP-1, which can exert phagocytosis of tagged target cells.[40] As shown in FIG. 4B, IFLs derived from either NK or T cells could promote Ramos cell elimination in the presence of THP-1 cells.

Figure 5A:
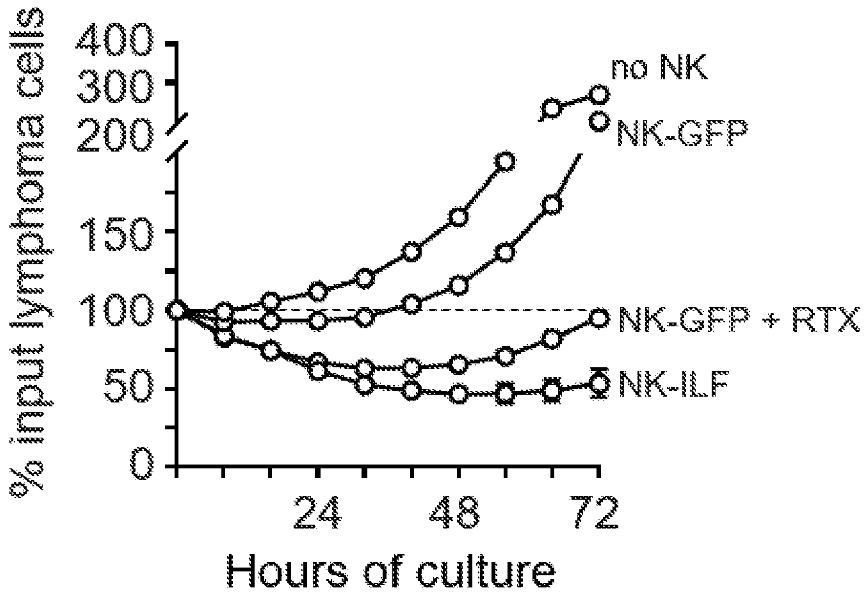
FIGS. 5A-C show ADCC mediated by immune cell-derived IFL.
Figure 5B:
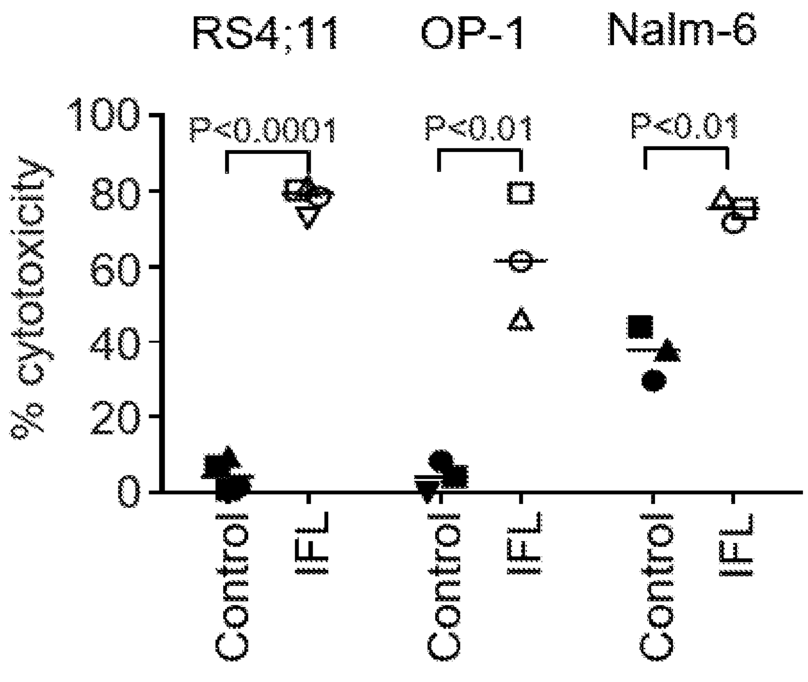
Figure 5C:
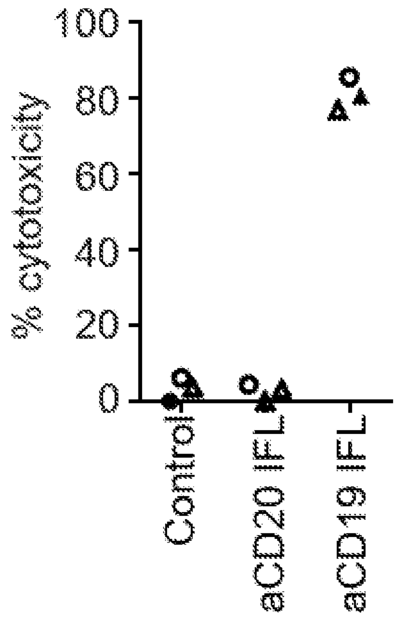

To determine whether IFLs produced by NK cells and T cells could mediate ADCC, we co-cultured CD20+ lymphoma cell line Raji with NK cells transduced with GFP alone or anti-CD20 IFL at a E:T 1:1 ratio, using rituximab at 1 μg/mL with NK-GFP cells as a control. As shown in FIG. 5A, IFL NK cells exerted powerful cytotoxicity. In other tests, we determined the cytotoxic capacity of NK cells transduced with anti-CD19 IFL against 3 CD19+ leukemic cells lines (RS4;11, OP-1 and Nalm-6). As shown in FIG. 5B, NK-IFL cells were significantly more powerful than NK cells transduced with GFP alone and cell killing against the CD19+CD20− cell line RS4;11 was mediated only by the anti-CD19 IFL (FIG. 5C).

T Cells Expressing CD16 Receptors Exert ADCC Through Self-Produced IFLs

Figure 6B:
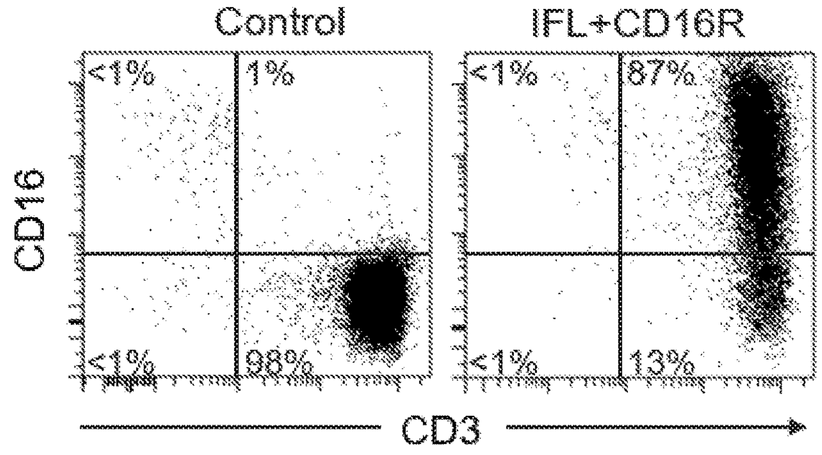
Figure 6C:
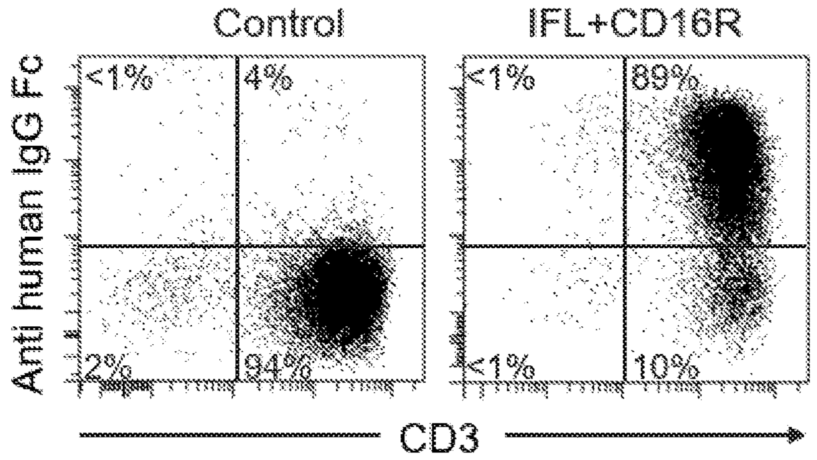
Figure 6D:
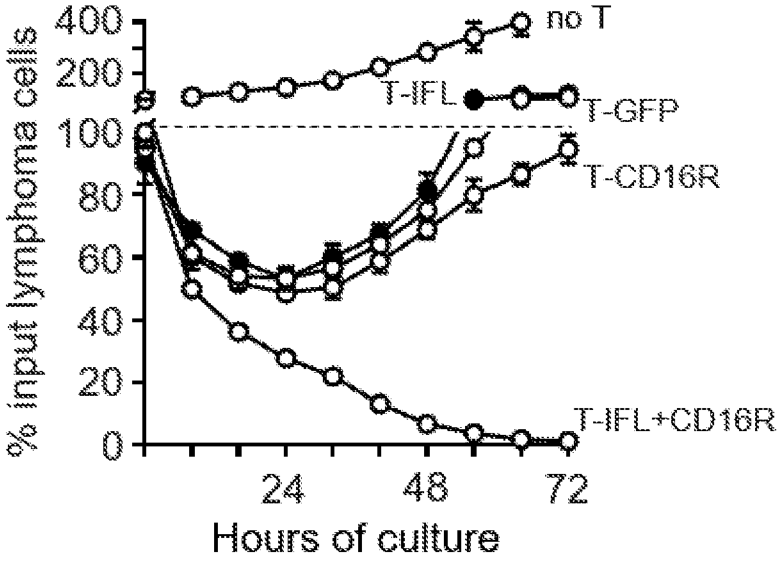

We prepared a bicistronic construct containing anti-CD20 IFL and the CD16 (V158)-41BB-CD3ζ receptor, separated by P2A (FIG. 6A). CD16-41BB-CD3 had been previously generated in our laboratory and shown to confer ADCC capacity to T lymphocytes.[32] We transduced T lymphocytes with the construct achieving expression of both components (FIG. 6B, C). When challenged against Ramos cells in long-term cultures, T lymphocytes expressing both IFL and CD16-41BB-CD3ζ eradicated lymphoma cells while T cell expressing only one of the genes, or GFP did not (FIG. 6D). Additional information regarding CD16-41BB-CD3ζ can be found U.S. Pat. No. 10,144,770 B2 and U.S. Patent Publication No. 2015/0139943, both of which are incorporated herein by reference in their entirety.

Figure 7A:
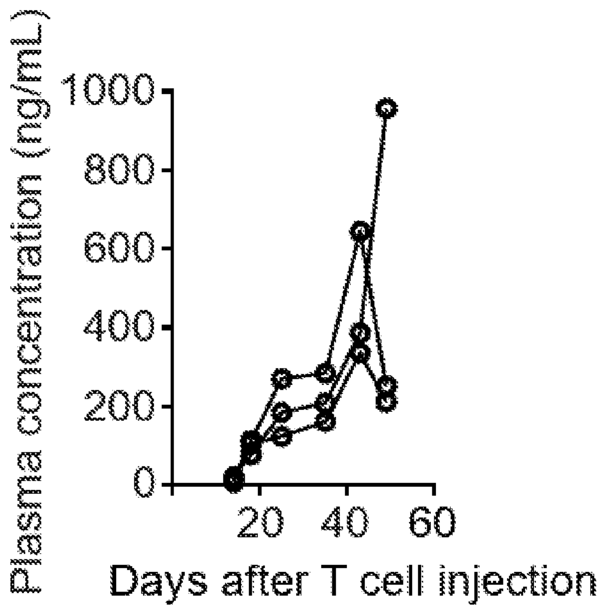
FIGS. 7A-B show plasma concentration and antitumor activity of IFL in vivo.
Figure 7B:
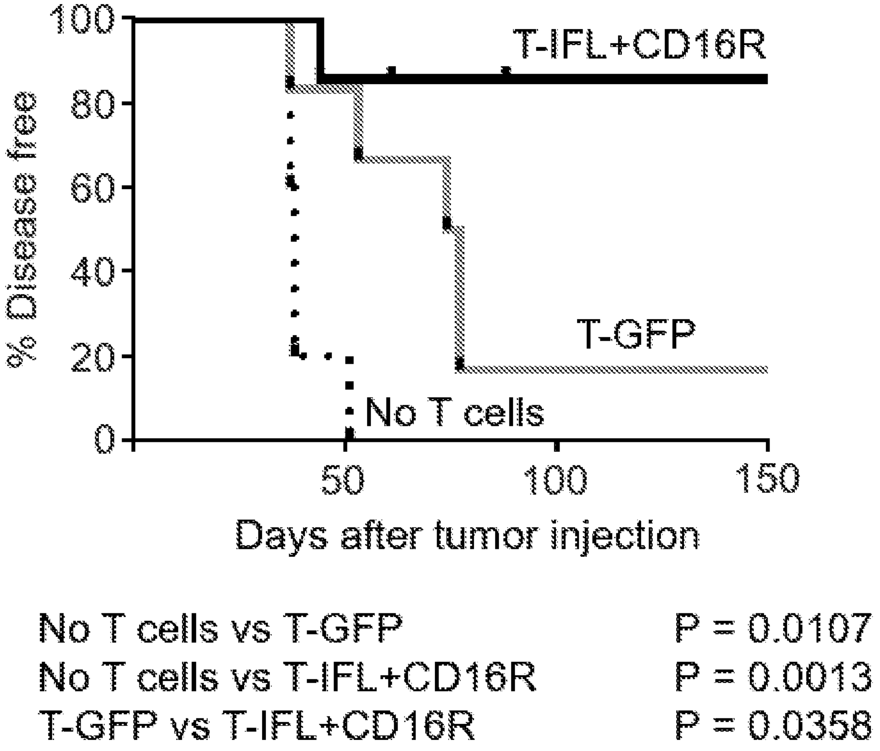

We next determined the levels of plasma IFL that can be measured in mouse plasma after intravenous injection of $2\times10^7$ T lymphocytes transduced with anti-CD20 IFL in NOD-SCID-IL2RGnull immunodeficient mice. As shown in FIG. 7A, IFL could be detected in plasma 50 days after cell injection, indicating the IFL secretion is durable. We assessed whether T lymphocytes expressing both IFL and CD16-41BB-CD3ζ could exert anti-tumor activity NOD-SCID-IL2RGnull immunodeficient mice engrafted with the CD20+ B-cell lymphoma cell line Daudi intraperitoneally. After intraperitoneal injection of T cells, there was a strong anti-tumor activity in mice receiving those with IFL and CD16-41BB-CD3 while tumor grew rapidly in those receiving T cells transduced with GFP only or no T cells (FIG. 7B).

Modified IFLs

The IFL constructs were modified to enhance some its functions and/or widen the range of its specificities. For example, the modified Fc can be further altered to increase its affinity for Fc receptors in NK cells and macrophages, thus enhancing ADCC and ADCP, and/or to increase its capacity to fix complement. In particular, the modified IFLs of FIGS. 8A-D were constructed.

Figure 9A:
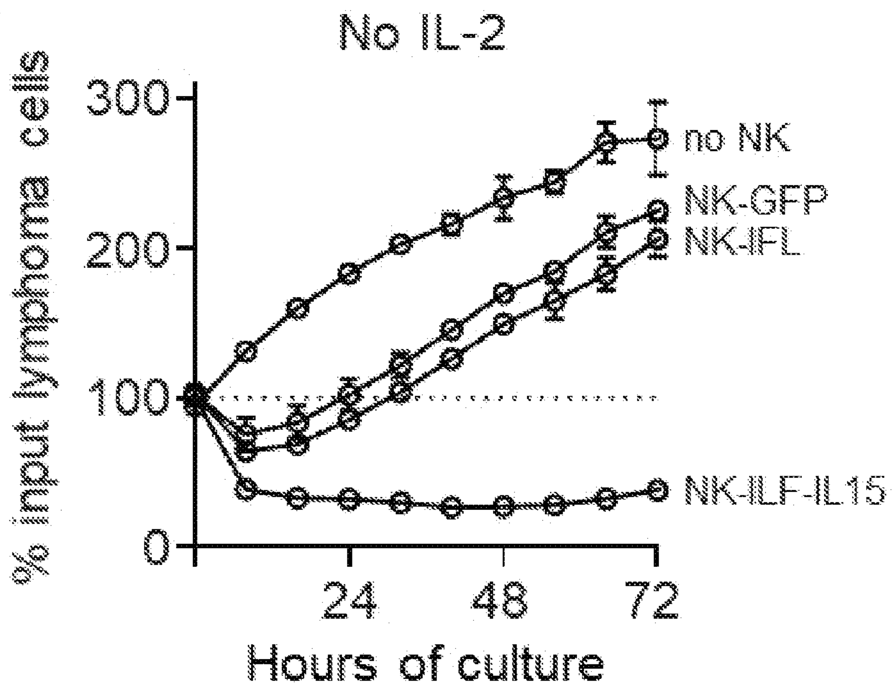
FIGS. 9A-B show ADCC mediated by anti-CD20 IFL linked to interleukin-15 (IL-15) (see FIG. 8C) and secreted by immune cells. The graphs show results of experiments in which the CD20+ lymphoma cells Ramos were cultured with NK cells transduced with GFP alone ("NK-GFP"), anti-CD20 IFL ("NK-IFL") or anti-CD20 IFL linked to IL-15 ("NK-IFL-IL15") at a 1:1 E:T ratio. As a control, Ramos cells were cultured without NK cells ("no NK"). In the experiment of FIG. 9A, IL-2 was not added; in the experiment of FIG. 9B, cultures were performed with 40 IU/mL IL-2. The number of viable Ramos cells was counted every 8 hours for 72 hours using life-cell imaging measured with an Incucyte System instrument.
Figure 9B:
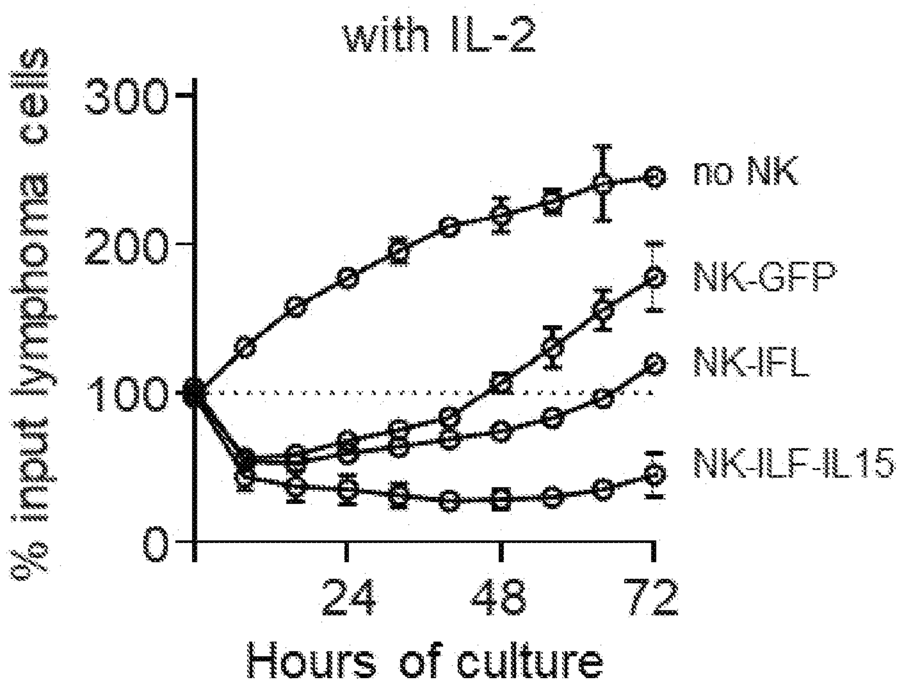

The results of the experiments shown in FIGS. 9A-B demonstrate that the addition of a sequence encoding IL-15 to the anti-CD20 IFL secreted by NK cells markedly increases the killing activity against CD20+ lymphoma cells in 3-day co-cultures. In these experiments, Ramos cell numbers were maximally reduced when NK cells were transduced with IFL-IL15; these cells were more powerful that those transduced with ILF lacking IL-15, which in turn were more powerful than NK cells transduced with GFP alone. The superiority of IFL-IL15 was observed regardless of whether IL-2 was present in the cultures. These results demonstrate that the function of IFLs can be augmented by linking them to other functional molecules.

Additional Embodiments

1. A peptide comprising:
   a) a single-chain variable fragment (scFv) domain;
   b) a fragment crystallizable (Fc) domain; and
   c) a hinge domain joining the scFv and Fe domains.
2. The peptide of Embodiment 1, wherein the scFv domain comprises an immunoglobulin variable light ($V_L$) domain, an immunoglobulin variable heavy ($V_H$) domain, and a linker domain joining the $V_L$ and $V_H$ domains.
3. The peptide of Embodiment 2, wherein the linker domain is $(G4S)_x$, wherein x is an integer from 1 to 100.
4. The peptide of Embodiment 3, wherein the linker domain is $(G4S)_3$.
5. The peptide of any one of Embodiments 1 through 4, wherein the scFv domain binds CD19.
6. The peptide of any one of Embodiments 1 through 4, wherein the scFv domain binds CD20.
7. The peptide of any one of Embodiments 1 through 4, wherein the scFv domain binds CD22, CD38, CD7, CD2, CD3, epidermal growth factor receptor (EGFR), CD123, CD33, B-cell maturation antigen (BCMA), mesothelin, human epidermal growth factor receptor 2 (Her2), prostate-specific membrane antigen (PSMA), disialoganglioside (GD2), PD-L1 (CD274), CD80 or CD86.
8. The peptide of any one of Embodiments 1 through 4, wherein the Fc domain comprises an immunoglobulin constant heavy 2 ($C_H2$) domain and an immunoglobulin constant heavy 3 ($C_H3$) domain.
9. The peptide of any one of Embodiments 1 through 4, wherein the Fc domain is human IgG1 Fc domain.
10. The peptide of any one of Embodiments 1 through 4, further comprising a signal peptide that is N-terminal to the scFv domain.
11. The peptide of any one of Embodiments 1 through 4, further comprising a self-cleaving peptide joining the Fc domain to a chimeric receptor, wherein the chimeric receptor comprises a receptor domain, a hinge and transmembrane domain, a co-stimulatory signaling domain, and a cytoplasmic signaling domain.
12. The peptide of Embodiment 11, wherein the self-cleaving peptide is a 2A peptide.
13. The peptide of Embodiment 11, wherein the receptor domain is CD16.
14. The peptide of Embodiment 11, wherein the hinge and transmembrane domain is a CD8a hinge and transmembrane domain.
15. The peptide of Embodiment 11, wherein the co-stimulatory domain is 4-1BB co-stimulatory domain.
16. The peptide of Embodiment 11, wherein the cytoplasmic signaling domain is a CD3ζ cytoplasmic signaling.
17. The peptide of Embodiment 11, wherein the chimeric receptor is CD16V-4-1BB-CD3ζ.
18. The peptide of any one of Embodiments 1 through 4, wherein the scFv domain binds CD19 or CD20, the Fc domain is a human IgG1 Fc domain, and the hinge domain is an IgG1 hinge domain; the peptide further comprising a CD8a signal peptide that is N-terminal to the scFv domain; the peptide further comprising a chimeric receptor that is CD16V-4-1BB-CD3ζ.
19. The peptide of any one of Embodiments 1 through 4, further comprising one or more of the following mutations: S239D; S267E; H268F; or I332E.
20. The peptide of any one of Embodiments 1 through 4, further comprising one or more of the following mutations: E345K; E430G; or S440Y.
21. The peptide of any one of Embodiments 1 through 4, wherein the peptide further comprise IL-15 joined to the Fc domain by a linker.
22. The peptide of Embodiment 21, wherein the linker that joins IL-15 to the Fc domain is selected from the group consisting of SEQ ID NO: 52 and $A(EAAAK)_zA$ (SEQ ID NO: 55), wherein z is an integer from 2 to 5.
23. The peptide of any one of Embodiments 1 through 4, wherein the peptide further comprises a ligand that binds 4-1BB (CD37), CD28, or OX40 (CD134) joined to the Fc domain by a linker.
24. The peptide of Embodiment 23, wherein the linker that joins IL-15 to the Fc domain is selected from the group consisting of SEQ ID NO: 52 and $A(EAAAK)_zA$ (SEQ ID NO: 55), wherein z is an integer from 2 to 5.
25. A nucleic acid encoding the peptide of any of Embodiments 1 through 24.
26. A vector comprising a nucleic acid, the nucleic acid encoding the peptide of any of Embodiments 1 through 24.
27. The vector of Embodiment 26, wherein the vector is a murine stem cell virus (MSCV).
28. An immune cell that expresses a peptide, wherein the peptide comprises:
   a) a T-cell receptor (TCR) β domain;
   b) a first fragment crystallizable (Fc) domain joined to the TCR β domain;
   c) a TCR α domain;
   d) a self-cleaving peptide joining the Fc domain to the TCR α domain;
   e) a second Fc domain joined to the TCR α domain.
29. The immune cell of Embodiment 28, further comprising a signal peptide joined to the T-cell receptor (TCR) β domain.
30. The immune cell of Embodiment 28, wherein the first Fc domain is the same as the second Fc domain.
31. A peptide comprising:
   a) a T-cell receptor (TCR) β domain;
   b) a first fragment crystallizable (Fc) domain joined to the TCR β domain;
   c) a TCR α domain;

d) a self-cleaving peptide joining the Fc domain to the TCR α domain;

e) a second Fc domain joined to the TCR α domain.

32. The peptide of Embodiment 31, further comprising a signal peptide joined to the T-cell receptor (TCR) β domain.

33. The peptide of Embodiment 31, wherein the first Fc domain is the same as the second Fc domain.

34. A nucleic acid encoding the peptide of any one of Embodiments 31 through 33.

35. A vector comprising a nucleic acid, the nucleic acid encoding the peptide of any one of Embodiments 31 through 33.

36. A method of making a transgenic host cell, the method comprising introducing a vector into a host cell, the vector comprising a nucleic acid encoding the peptide of any of Embodiments 1 through 24 or Embodiments 31 through 33.

37. A method of enhancing antibody-dependent cell cytotoxicity (ADCC), antibody-dependent cell phagocytosis (ADCP), or complement-dependent cytotoxicity (CDC) in a subject, the method comprising administering to the subject a therapeutically effective amount of any of the immune cells described herein.

SEQUENCES

SEQ ID NO: 1: Anti-CD20 IFL, Rituximab signal peptide; cDNA:
ATGGACTTCCAGGTGCAGATCATCAGCTTTCTGCTGATCTCCGCCTCT SEQ ID NO: 2: Anti-CD20 IFL, Rituximab signal peptide; amino acid:
MDFQVQIISFLLISAS SEQ ID NO: 3: Anti-CD20 IFL, Immunoglobulin variable domain of rituximab light chain; cDNA:
GTGATCATGTCCAGGGGCCAGATCGTGCTGAGCCAGTCCCCAGCAATCCTGTCTG

CCAGCCCTGGAGAGAAGGTGACCATGACATGCCGCGCCAGCTCCTCTGTGAGCT

ACATCCACTGGTTCCAGCAGAAGCCCGGCAGCTCCCCTAAGCCCTGGATCTATGC

CACAAGCAACCTGGCCTCCGGCGTGCCTGTGCGGTTTTCCGGCTCTGGCAGCGGC

ACCTCCTACTCTCTGACAATCAGCAGAGTGGAGGCCGAGGATGCCGCCACCTACT

ATTGCCAGCAGTGGACCTCCAATCCCCCTACATTCGGCGGCGGCACCAAGCTGGA

GATCAAG

SEQ ID NO: 4: Anti-CD20 IFL, Immunoglobulin variable domain of rituximab light chain; amino acid:
VIMSRGQIVLSQSPAILSASPGEKVTMTCRASSSVSYIHWFQQKPGSSPKPWIYATSNL

ASGVPVRFSGSGSGTSYSLTISRVEAEDAATYYCQQWTSNPPTFGGGTKLEIK

SEQ ID NO: 5: Anti-CD20 IFL, Linker; cDNA:
GGCGGCGGCGGCTCTGGAGGAGGAGGCAGCGGCGGAGGAGGCTCC SEQ ID NO: 6: Anti-CD20 IFL, Linker; amino acid:
GGGGSGGGGSGGGGS SEQ ID NO: 7: Anti-CD20 IFL, Immunoglobulin variable domain of rituximab heavy chain; cDNA:

CAGGTGCAGCTGCAGCAGCCAGGAGCAGAGCTGGTGAAGCCAGGAGCCTCTGTG

AAGATGAGCTGTAAGGCCTCCGGCTACACCTTCACAAGCTATAACATGCACTGG

GTGAAGCAGACACCAGGAAGGGGCCTGGAGTGGATCGGAGCAATCTACCCTGGC

AACGGCGACACCTCCTATAATCAGAAGTTTAAGGGCAAGGCCACCCTGACAGCC

GATAAGTCTAGCTCCACAGCCTACATGCAGCTGTCTAGCCTGACCTCTGAGGACA

GCGCCGTGTACTATTGCGCCAGAAGCACATACTATGGCGGCGATTGGTACTTCAA

CGTGTGGGGAGCAGGCACCACAGTGACCGTGTCTGCC

SEQ ID NO: 8: Anti-CD20 IFL, Immunoglobulin variable domain of rituximab heavy chain; amino acid:
QVQLQQPGAELVKPGASVKMSCKASGYTFTSYNMHWVKQTPGRGLEWIGAIYPGN

GDTSYNQKFKGKATLTADKSSSTAYMQLSSLTSEDSAVYYCARSTYYGGDWYFNV

WGAGTTVTVSA

-continued

SEQ ID NO: 9: Anti-CD20 IFL, Hinge and constant heavy domain 2 and 3 of immunoglobulin G1; cDNA:
GAGCCAAAGAGCTGTGACAAGACCCACACATGCCCACCATGTCCAGCACCTGAG

CTGCTGGGAGGACCTTCCGTGTTCCTGTTTCCTCCAAAGCCAAAGGATACCCTGA

TGATCTCTAGGACCCCTGAGGTGACATGCGTGGTGGTGGACGTGAGCCACGAGG

ACCCCGAGGTGAAGTTTAACTGGTACGTGGACGGCGTGGAGGTGCACAATGCCA

AGACCAAGCCTCGGGAGGAGCAGTACAACTCCACATATAGAGTGGTGTCTGTGC

TGACCGTGCTGCACCAGGATTGGCTGAACGGCAAGGAGTATAAGTGCAAGGTGT

CCAATAAGGCCCTGCCAGCCCCCATCGAGAAGACAATCTCTAAGGCCAAGGGCC

AGCCTAGGGAGCCACAGGTGTACACCCTGCCACCTTCCCGCGACGAGCTGACAA

AGAACCAGGTGTCTCTGACCTGTCTGGTGAAGGGCTTCTATCCATCTGACATCGC

CGTGGAGTGGGAGAGCAATGGCCAGCCCGAGAACAATTACAAGACCACACCACC

CGTGCTGGACTCCGATGGCTCTTTCTTTCTGTATAGCAAGCTGACAGTGGACAAG

TCCCGGTGGCAGCAGGGCAACGTGTTTAGCTGTTCCGTGATGCACGAGGCCCTGC

ACAATCACTACACCCAGAAGTCTCTGAGCCTGTCCCCCGGCAAGTGA

SEQ ID NO: 10: Anti-CD20 IFL, Hinge and constant heavy domain 2 and 3 of immunoglobulin G1; amino acid:
EPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSL

SLSPGK

SEQ ID NO: 11: Anti-CD19 IFL, CD8α signal peptide; cDNA:
ATGGCCTTACCAGTGACCGCCTTGCTCCTGCCGCTGGCCTTGCTGCTCCACGCCG

CCAGGCCG

SEQ ID NO: 12: Anti-CD19 IFL, CD8α signal peptide; amino acid:
MALPVTALLLPLALLLHAARP SEQ ID NO: 13: Anti-CD19 IFL, Immunoglobulin variable domain of light chain; cDNA:
GACATCCAGATGACACAGACTACATCCTCCCTGTCTGCCTCTCTGGGAGACAGAG

TCACCATCAGTTGCAGGGCAAGTCAGGACATTAGTAAATATTTAAATTGGTATCA

GCAGAAACCAGATGGAACTGTTAAACTCCTGATCTACCATACATCAAGATTACAC

TCAGGAGTCCCATCAAGGTTCAGTGGCAGTGGGTCTGGAACAGATTATTCTCTCA

CCATTAGCAACCTGGAGCAAGAAGATATTGCCACTTACTTTTGCCAACAGGGTAA

TACGCTTCCGTACACGTTCGGAGGGGGGACCAAGCTGGAGATCACA

SEQ ID NO: 14: Anti-CD19 IFL, Immunoglobulin variable domain of light chain; amino acid:
DIQMTQTTSSLSASLGDRVTISCRASQDISKYLNWYQQKPDGTVKLLIYHTSRLHSGV

PSRFSGSGSGTDYSLTISNLEQEDIATYFCQQGNTLPYTFGGGTKLEIT

SEQ ID NO: 15: Anti-CD19 IFL, Linker; cDNA:
GGTGGCGGTGGCTCGGGCGGTGGTGGGTCGGGTGGCGGCGGATCT SEQ ID NO: 16: Anti-CD19 IFL, Linker; amino acid:
GGGGSGGGGSGGGGS SEQ ID NO: 17: Anti-CD19 IFL, Immunoglobulin variable domain of heavy chain; cDNA:
GAGGTGAAACTGCAGGAGTCAGGACCTGGCCTGGTGGCGCCCTCACAGAGCCTG

TCCGTCACATGCACTGTCTCAGGGGTCTCATTACCCGACTATGGTGTAAGCTGGA

-continued

TTCGCCAGCCTCCACGAAAGGGTCTGGAGTGGCTGGGAGTAATATGGGGTAGTG

AAACCACATACTATAATTCAGCTCTCAAATCCAGACTGACCATCATCAAGGACAA

CTCCAAGAGCCAAGTTTTCTTAAAAATGAACAGTCTGCAAACTGATGACACAGCC

ATTTACTACTGTGCCAAACATTATTACTACGGTGGTAGCTATGCTATGGACTACT

GGGGCCAAGGAACCTCAGTCACCGTCTCCTCA

SEQ ID NO: 18: Anti-CD19 IFL, Immunoglobulin variable domain of heavy chain; amino acid:
EVKLQESGPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAMDYWGQ

GTSVTVSS

SEQ ID NO: 19: Anti-CD19 IFL, Hinge and constant heavy domain 2 and 3 of immunoglobulin G1; cDNA:
GAGCCAAAGAGCTGTGACAAGACCCACACATGCCCACCATGTCCAGCACCTGAG

CTGCTGGGAGGACCTTCCGTGTTCCTGTTTCCTCCAAAGCCAAAGGATACCCTGA

TGATCTCTAGGACCCCTGAGGTGACATGCGTGGTGGTGGACGTGAGCCACGAGG

ACCCCGAGGTGAAGTTTAACTGGTACGTGGACGGCGTGGAGGTGCACAATGCCA

AGACCAAGCCTCGGGAGGAGCAGTACAACTCCACATATAGAGTGGTGTCTGTGC

TGACCGTGCTGCACCAGGATTGGCTGAACGGCAAGGAGTATAAGTGCAAGGTGT

CCAATAAGGCCCTGCCAGCCCCCATCGAGAAGACAATCTCTAAGGCCAAGGGCC

AGCCTAGGGAGCCACAGGTGTACACCCTGCCACCTTCCCGCGACGAGCTGACAA

AGAACCAGGTGTCTCTGACCTGTCTGGTGAAGGGCTTCTATCCATCTGACATCGC

CGTGGAGTGGGAGAGCAATGGCCAGCCCGAGAACAATTACAAGACCACACCACC

CGTGCTGGACTCCGATGGCTCTTTCTTTCTGTATAGCAAGCTGACAGTGGACAAG

TCCCGGTGGCAGCAGGGCAACGTGTTTAGCTGTTCCGTGATGCACGAGGCCCTGC

ACAATCACTACACCCAGAAGTCTCTGAGCCTGTCCCCCGGCAAGTGA

SEQ ID NO: 20: Anti-CD19 IFL, Hinge and constant heavy domain 2 and 3 of immunoglobulin G1; amino acid:
EPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSL

SLSPGK

SEQ ID NO: 21: Anti-CD20 IFL-P2A-CD16V-BB-ζ Rituximab signal peptide; cDNA:
ATGGATTTCCAGGTCCAGATTATTTCCTTCCTGCTGATTAGTGCCAGT SEQ ID NO: 22: Anti-CD20 IFL-P2A-CD16V-BB-ζ Rituximab signal peptide; amino acid:
MDFQVQIISFLLISAS SEQ ID NO: 23: Anti-CD20 IFL-P2A-CD16V-BB-ζ Immunoglobulin variable domain of rituximab light chain; cDNA:
GTGATTATGAGTAGAGGCCAGATTGTGCTGAGCCAGTCCCCAGCAATCCTGAGC

GCCTCCCCAGGAGAGAAGGTGACAATGACCTGCAGAGCCAGCTCCTCTGTGAGC

TACATCCACTGGTTCCAGCAGAAGCCCGGCAGCTCCCCAAAGCCCTGGATCTATG

CCACCTCCAACCTGGCCTCTGGCGTGCCTGTGAGATTTTCTGGCAGCGGCTCCGG

CACATCTTACAGCCTGACCATCAGCAGGGTGGAGGCAGAGGACGCAGCAACCTA

CTATTGCCAGCAGTGGACATCCAATCCCCCTACCTTCGGCGGCGGCACAAAGCTG

GAGATCAAGGGC

-continued

SEQ ID NO: 24: Anti-CD20 IFL-P2A-CD16V-BB-ζ Immunoglobulin variable domain of rituximab light chain; amino acid:
VIMSRGQIVLSQSPAILSASPGEKVTMTCRASSSVSYIHWFQQKPGSSPKPWIYATSNL

ASGVPVRFSGSGSGTSYSLTISRVEAEDAATYYCQQWTSNPPTFGGGTKLEIK

SEQ ID NO: 25: Anti-CD20 IFL-P2A-CD16V-BB-ζ Linker; cDNA:
GGCGGCGGCTCTGGAGGAGGAGGAAGCGGAGGAGGAGGCTCC SEQ ID NO: 26: Anti-CD20 IFL-P2A-CD16V-BB-ζ Linker; amino acid:
GGGGSGGGGSGGGGS SEQ ID NO: 27: Anti-CD20 IFL-P2A-CD16V-BB-ζ Immunoglobulin variable domain of rituximab heavy chain; cDNA:
CAGGTGCAGCTGCAGCAGCCTGGAGCAGAGCTGGTGAAGCCAGGAGCCAGCGTG

AAGATGTCCTGTAAGGCCTCTGGCTACACATTCACCAGCTATAACATGCACTGGG

TGAAGCAGACCCCAGGAAGAGGCCTGGAGTGGATCGGAGCCATCTACCCTGGCA

ACGGCGACACATCCTATAATCAGAAGTTTAAGGGCAAGGCCACACTGACCGCCG

ATAAGTCTAGCTCCACCGCCTACATGCAGCTGTCTAGCCTGACATCCGAGGACTC

TGCCGTGTACTATTGCGCCAGGAGCACCTACTATGGCGGCGATTGGTACTTCAAC

GTGTGGGGCGCCGGCACCACAGTGACAGTGTCTGCC

SEQ ID NO: 28: Anti-CD20 IFL-P2A-CD16V-BB-ζ Immunoglobulin variable domain of rituximab heavy chain; amino acid:
QVQLQQPGAELVKPGASVKMSCKASGYTFTSYNMHWVKQTPGRGLEWIGAIYPGN

GDTSYNQKFKGKATLTADKSSSTAYMQLSSLTSEDSAVYYCARSTYYGGDWYFNV

WGAGTTVTVSA

SEQ ID NO: 29: Anti-CD20 IFL-P2A-CD16V-BB-ζ Hinge and constant heavy domain 2 and 3 of immunoglobulin G1; cDNA:
GAGCCCAAGAGCTGTGACAAGACACACACCTGCCCACCATGTCCTGCACCAGAG

CTGCTGGGAGGACCATCCGTGTTCCTGTTTCCTCCAAAGCCCAAGGATACCCTGA

TGATCTCTCGCACACCTGAGGTGACCTGCGTGGTGGTGGACGTGAGCCACGAGG

ATCCAGAGGTGAAGTTTAACTGGTACGTGGACGGCGTGGAGGTGCACAATGCCA

AGACCAAGCCTAGAGAGGAGCAGTACAACAGCACCTATAGGGTGGTGTCCGTGC

TGACAGTGCTGCACCAGGATTGGCTGAACGGCAAGGAGTATAAGTGCAAGGTGT

CCAATAAGGCCCTGCCCGCCCCTATCGAGAAGACCATCTCTAAGGCAAAGGGAC

AGCCAAGGGAGCCACAGGTGTACACACTGCCCCCTAGCCGGGACGAGCTGACCA

AGAACCAGGTGTCCCTGACATGTCTGGTGAAGGGCTTCTATCCATCCGATATCGC

CGTGGAGTGGGAGTCTAATGGCCAGCCCGAGAACAATTACAAGACCACACCACC

CGTGCTGGACAGCGATGGCTCCTTCTTTCTGTATTCTAAGCTGACCGTGGACAAG

AGCCGGTGGCAGCAGGGCAACGTGTTCTCCTGCTCTGTGATGCACGAGGCCCTGC

ACAATCACTACACCCAGAAGAGCCTGTCCCTGTCTCCCGGCAAG

SEQ ID NO: 30: Anti-CD20 IFL-P2A-CD16V-BB-ζ Hinge and constant heavy domain 2 and 3 of immunoglobulin G1; amino acid:
EPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSL

SLSPGK

SEQ ID NO: 31: Anti-CD20 IFL-P2A-CD16V-BB-ζ P2A; cDNA:
GCCACAAACTTTAGCCTGCTGAAGCAGGCAGGCGACGTGGAGGAGAATCCAGGA -continued SEQ ID NO: 32: Anti-CD20 IFL-P2A-CD16V-BB-ζ P2A; amino acid:
ATNFSLLKQAGDVEENPG SEQ ID NO: 33: Anti-CD20 IFL-P2A-CD16V-BB-ζ CD8α signal peptide; cDNA:
CCCGCCCTGCCAGTGACCGCCCTGCTGCTGCCTCTGGCCCTGCTGCTGCACGCAG

CCCGCCCA

SEQ ID NO: 34: Anti-CD20 IFL-P2A-CD16V-BB-ζ CD8α signal peptide; amino acid:
PALPVTALLLPLALLLHAARP SEQ ID NO: 35: Anti-CD20 IFL-P2A-CD16V-BB-ζ FCGR3A extracellular domain; cDNA:
GGCATGCGGACAGAGGATCTGCCCAAGGCCGTGGTGTTTCTGGAGCCTCAGTGG

TACCGCGTGCTGGAGAAGGACTCCGTGACCCTGAAGTGTCAGGGCGCCTATTCCC

CTGAGGATAACTCTACACAGTGGTTCCACAATGAGTCTCTGATCTCCTCTCAGGC

CAGCTCCTACTTTATCGACGCAGCAACCGTGGACGATAGCGGAGAGTATCGGTG

CCAGACAAACCTGTCTACCCTGAGCGATCCAGTGCAGCTGGAGGTGCACATCGG

ATGGCTGCTGCTGCAGGCACCTAGATGGGTGTTCAAGGAGGAGGATCCAATCCA

CCTGAGGTGTCACAGCTGGAAGAATACCGCCCTGCACAAGGTGACATACCTGCA

GAACGGCAAGGGCCGCAAGTACTTCCACCACAATTCCGACTTTTATATCCCAAAG

GCCACCCTGAAGGATAGCGGCTCCTATTTTTGCCGGGGCCTGGTGGGCTCCAAGA

ACGTGTCTAGCGAGACAGTGAATATCACAATCACCCAGGGCCTGGCCGTGTCTAC

AATCTCCTCTTTCTTTCCTCCAGGCTACCAG

SEQ ID NO: 36: Anti-CD20 IFL-P2A-CD16V-BB-ζ FCGR3A extracellular domain; amino acid:
GMRTEDLPKAVVFLEPQWYRVLEKDSVTLKCQGAYSPEDNSTQWFHNESLISSQASS

YFIDAATVDDSGEYRCQTNLSTLSDPVQLEVHIGWLLLQAPRWVFKEEDPIHLRCHS

WKNTALHKVTYLQNGKGRKYFHHNSDFYIPKATLKDSGSYFCRGLVGSKNVSSETV

NITITQGLAVSTISSFFPPGYQ

SEQ ID NO: 37: Anti-CD20 IFL-P2A-CD16V-BB-ζ CD8α hinge and transmembrane; cDNA:
ACCACAACCCCTGCACCAAGACCCCCTACACCAGCACCTACCATCGCAAGCCAG

CCACTGTCCCTGCGGCCCGAGGCCTGTAGGCCAGCAGCAGGAGGAGCAGTGCAC

ACCAGGGGCCTGGACTTCGCCTGCGATATCTATATCTGGGCACCTCTGGCAGGAA

CCTGTGGCGTGCTGCTGCTGAGCCTGGTCATCACCCTGTACTGC

SEQ ID NO: 38: Anti-CD20 IFL-P2A-CD16V-BB-ζ CD8α hinge and transmembrane; amino acid:
TTTPAPRPPTPAPTIASQPLSLRPEACRPAAGGAVHTRGLDFACDIYIWAPLAGTCGV

LLLSLVITLYC

SEQ ID NO: 39: Anti-CD20 IFL-P2A-CD16V-BB-ζ CD137 cytoplasmic domain; cDNA:
AAGAGAGGCAGGAAGAAGCTGCTGTATATCTTCAAGCAGCCTTTTATGCGCCCA

GTGCAGACAACCCAGGAGGAGGACGGCTGCTCCTGTCGGTTCCCAGAAGAGGAG

GAGGGAGGATGTGAGCTG

SEQ ID NO: 40: Anti-CD20 IFL-P2A-CD16V-BB-ζ CD137 cytoplasmic domain; amino acid:
KRGRKKLLYIFKQPFMRPVQTTQEEDGCSCRFPEEEEGGCEL SEQ ID NO: 41: Anti-CD20 IFL-P2A-CD16V-BB-ζ CD3ζ cytoplasmic domain; cDNA:
AGGGTGAAGTTTTCTCGGAGCGCCGATGCACCAGCATACCAGCAGGGACAGAAC

CAGCTGTATAACGAGCTGAATCTGGGCCGGAGAGAGGAGTACGACGTGCTGGAT

-continued

AAGAGGCGCGGCAGGGACCCCGAGATGGGAGGCAAGCCCCGGAGAAAGAACCC

TCAGGAGGGCCTGTACAATGAGCTGCAGAAGGACAAGATGGCCGAGGCCTATAG

CGAGATCGGCATGAAGGGAGAGAGGCGCCGGGGCAAGGGACACGATGGCCTGT

ACCAGGGCCTGTCAACAGCAACAAAAGACACTTACGACGCACTGCACATGCAGG

CTCTGCCCCCAAGATAA

SEQ ID NO: 42: Anti-CD20 IFL-P2A-CD16V-BB-ζ CD3ζ cytoplasmic domain; amino acid:
RVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALP

PR

SEQ ID NO: 43: P2A cDNA:
GCCACAAACTTTAGCCTGCTGAAGCAGGCAGGCGACGTGGAGGAGAATCCAGGA

SEQ ID NO: 44: P2A amino acid:
ATNFSLLKQAGDVEENPG

SEQ ID NO: 45: T2A cDNA:
GGAAGCGGAGAGGGCAGAGGAAGTCTGCTAACATGCGGTGACGTCGAGGAGAA

TCCTGGACCT

SEQ ID NO: 46: T2A amino acid:
GSGEGRGSLLTCGDVEENPGP

SEQ ID NO: 47: E2A cDNA:
GGAAGCGGACAGTGTACTAATTATGCTCTCTTGAAATTGGCTGGAGATGTTGAGA

GCAACCCTGGACCT

SEQ ID NO: 48: E2A amino acid:
GSGQCTNYALLKLAGDVESNPGP

SEQ ID NO: 49: F2A cDNA:
GGAAGCGGAGTGAAACAGACTTTGAATTTTGACCTTCTCAAGTTGGCGGGAGAC

GTGGAGTCCAACCCTGGACCT

SEQ ID NO: 50: F2A amino acid:
GSGVKQTLNFDLLKLAGDVESNPGP

SEQ ID NO: 51: Linker of FIG. 8C nucleotide:
AGCTGCTGCTAAGGCACTGGAAGCAGAAGCCGCGGCTAAGGAGGCGGCTGCAAA

AGAAGCTGCAGCCAAGGAAGCAGCCGCGAAGGCA

SEQ ID NO: 52: Linker of FIG. 8C amino acid:
AEAAAKEAAAKEAAAKEAAAKALEAEAAAKEAAAKEAAAKEAAAKA SEQ ID NO: 53: IL-15 of FIG. 8C nucleotide:
AACTGGGTGAATGTGATCTCCGACCTGAAGAAGATCGAGGATCTGATCCAGTCT

ATGCACATCGACGCCACCCTGTACACAGAGTCCGATGTGCACCCCTCTTGCAAGG

TGACCGCCATGAAGTGTTTTCTGCTGGAGCTGCAGGTCATCTCCCTGGAGTCTGG

CGACGCCAGCATCCACGATACAGTGGAGAACCTGATCATCCTGGCCAACAATTCT

CTGTCCTCTAACGGCAATGTGACCGAGAGCGGCTGCAAGGAGTGTGAGGAGCTG

GAGGAGAAGAATATCAAAGAGTTCCTGCAGAGTTTCGTCCATATCGTCCAGATGT

TTATCAATACCTCC

SEQ ID NO: 54: IL-15 of FIG. 8C amino acid:
NWVNVISDLKKIEDLIQSMHIDATLYTESDVHPSCKVTAMKCFLLELQVISLESGDAS

IHDTVENLIILANNSLSSNGNVTESGCKECEELEEKNIKEFLQSFVHIVQMFINTS

INCORPORATION BY REFERENCE; EQUIVALENTS

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

REFERENCES

1. Yu A L, Gilman A L, Ozkaynak M F, et al. Anti-GD2 antibody with G M-CSF, interleukin-2, and isotretinoin for neuroblastoma. N Engl J Med. 2010; 363(14):1324-1334.
2. Ferris R L, Jaffee E M, Ferrone S. Tumor antigen-targeted, monoclonal antibody-based immunotherapy: clinical response, cellular immunity, and immunoescape. J Clin Oncol. 2010; 28(28):4390-4399.
3. Maloney D G. Anti-CD20 antibody therapy for B-cell lymphomas. N Engl J Med. 2012; 366(21):2008-2016.
4. Scott A M, Wolchok J D, Old U. Antibody therapy of cancer. Nat Rev Cancer. 2012; 12(4):278-287.
5. Weiner L M, Murray J C, Shuptrine C W. Antibody-based immunotherapy of cancer. Cell. 2012; 148(6):1081-1084.
6. Galluzzi L, Vacchelli E, Fridman W H, et al. Trial Watch: Monoclonal antibodies in cancer therapy. Oncoimmunology. 2012; 1(1):28-37.
7. Nimmerjahn F, Ravetch J V. Fcgamma receptors as regulators of immune responses. Nat Rev Immunol. 2008; 8(1):34-47.
8. Koene H R, Kleijer M, Algra J, Roos D, von dem Borne A E, de Haas M. Fc gammaRIIIa-158V/F polymorphism influences the binding of IgG by natural killer cell Fc gammaRIIIa, independently of the Fc gammaRIIIa-48L/R/H phenotype. Blood. 1997; 90(3):1109-1114.
9. Cartron G, Dacheux L, Salles G, et al. Therapeutic activity of humanized anti-CD20 monoclonal antibody and polymorphism in IgG Fc receptor FcgammaRIIIa gene. Blood. 2002; 99(3):754-758.
10. Weng W K, Levy R. Two immunoglobulin G fragment C receptor polymorphisms independently predict response to rituximab in patients with follicular lymphoma. J Clin Oncol. 2003; 21(21):3940-3947.
11. Dall'Ozzo S, Tartas S, Paintaud G, et al. Rituximab-dependent cytotoxicity by natural killer cells: influence of FCGR3A polymorphism on the concentration-effect relationship. Cancer Res. 2004; 64(13):4664-4669.
12. Hatjiharissi E, Xu L, Santos D D, et al. Increased natural killer cell expression of CD16, augmented binding and ADCC activity to rituximab among individuals expressing the Fc{gamma}RIIIa-158 V/V and V/F polymorphism. Blood. 2007; 110(7):2561-2564.
13. Musolino A, Naldi N, Bortesi B, et al. Immunoglobulin G fragment C receptor polymorphisms and clinical efficacy of trastuzumab-based therapy in patients with HER-2/neu-positive metastatic breast cancer. J Clin Oncol. 2008; 26(11):1789-1796.
14. Bibeau F, Lopez-Crapez E, Di Fiore F, et al. Impact of Fc{gamma}RIIa-Fc{gamma}RIIIa polymorphisms and KRAS mutations on the clinical outcome of patients with metastatic colorectal cancer treated with cetuximab plus irinotecan. J Clin Oncol. 2009; 27(7):1122-1129.
15. Ahlgrimm M, Pfreundschuh M, Kreuz M, Regitz E, Preuss K D, Bittenbring J. The impact of Fc-gamma receptor polymorphisms in elderly patients with diffuse large B-cell lymphoma treated with CHOP with or without rituximab. Blood. 2011; 118(17):4657-4662.
16. Veeramani S, Wang S Y, Dahle C, et al. Rituximab infusion induces N K activation in lymphoma patients with the high-affinity CD16 polymorphism. Blood. 2011; 118(12):3347-3349.
17. Weiskopf K, Weissman I L. Macrophages are critical effectors of antibody therapies for cancer. MAbs. 2015; 7(2):303-310.
18. Kochenderfer I N, Wilson W H, Janik J E, et al. Eradication of B-lineage cells and regression of lymphoma in a patient treated with autologous T cells genetically engineered to recognize CD19. Blood. 2010; 116 (20):4099-4102.
19. Porter D L, Levine B L, Kalos M, Bagg A, June C H. Chimeric antigen receptor-modified T cells in chronic lymphoid leukemia. N Engl J Med. 2011; 365(8):725-733.
20. Maude S L, Frey N, Shaw P A, et al. Chimeric antigen receptor T cells for sustained remissions in leukemia. N Engl J Med. 2014; 371(16):1507-1517.
21. Davila M L, Riviere I, Wang X, et al. Efficacy and Toxicity Management of 19-28z CAR T Cell Therapy in B Cell Acute Lymphoblastic Leukemia. Sci Transl Med. 2014; 6(224):224ra225.
22. Kochenderfer J N, Dudley M E, Kassim S H, et al. Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor. J Clin Oncol. 2014.
23. Lee D W, Kochenderfer I N, Stetler-Stevenson M, et al. T cells expressing CD19 chimeric antigen receptors for acute lymphoblastic leukaemia in children and young adults: a phase 1 dose-escalation trial. Lancet. 2014.
24. Turtle C J, Hanafi L A, Berger C, et al. CD19 CAR-T cells of defined CD4+:CD8+ composition in adult B cell ALL patients. J Clin Invest. 2016; 126(6):2123-2138.
25. Sadelain M, Riviere I, Riddell S. Therapeutic T cell engineering. Nature. 2017; 545(7655):423-431.
26. Maude S L, Laetsch T W, Buechner J, et al. Tisagenlecleucel in Children and Young Adults with B-Cell Lymphoblastic Leukemia. N Engl J Med. 2018; 378(5):439-448.
27. Eshhar Z, Waks T, Gross G, Schindler D G. Specific activation and targeting of cytotoxic lymphocytes through chimeric single chains consisting of antibody-binding domains and the gamma or zeta subunits of the immunoglobulin and T-cell receptors. Proc Natl Acad Sci USA. 1993; 90(2):720-724.
28. Geiger T L, Leitenberg D, Flavell R A. The TCR zeta-chain immunoreceptor tyrosine-based activation motifs are sufficient for the activation and differentiation of primary T lymphocytes. J Immunol. 1999; 162(10):5931-5939.
29. Brentjens R J, Latouche J B, Santos E, et al. Eradication of systemic B-cell tumors by genetically targeted human T lymphocytes co-stimulated by CD80 and interleukin-15. Nat Med. 2003; 9(3):279-286.
30. Cooper L J, Topp M S, Serrano L M, et al. T-cell clones can be rendered specific for CD19: toward the selective augmentation of the graft-versus-B-lineage leukemia effect. Blood. 2003; 101(4):1637-1644.
31. Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia. 2004; 18:676-684.
32. Kudo K, Imai C, Lorenzini P, et al. T lymphocytes expressing a CD16 signaling receptor exert antibody-dependent cancer cell killing. Cancer Res. 2014; 74(1): 93-103.
33. Manabe A, Coustan-Smith E, Kumagai M, et al. Interleukin-4 induces programmed cell death (apoptosis) in cases of high-risk acute lymphoblastic leukemia. Blood. 1994; 83(7):1731-1737.
34. Imai C, Iwamoto S, Campana D. Genetic modification of primary natural killer cells overcomes inhibitory signals and induces specific killing of leukemic cells. Blood. 2005; 106:376-383.
35. Fujisaki H, Kakuda H, Shimasaki N, et al. Expansion of highly cytotoxic human natural killer cells for cancer cell therapy. Cancer Res. 2009; 69(9):4010-4017.
36. Holst J, Szymczak-Workman A L, Vignali K M, Burton A R, Workman C J, Vignali D A. Generation of T-cell receptor retrogenic mice. Nat Protoc. 2006; 1(1):406-417.
37. Shimasaki N, Campana D. Natural killer cell reprogramming with chimeric immune receptors. Methods Mol Biol. 2013; 969:203-220.
38. Chao M P, Alizadeh A A, Tang C, et al. Anti-CD47 antibody synergizes with rituximab to promote phagocytosis and eradicate non-Hodgkin lymphoma. Cell. 2010; 142(5):699-713.
39. Hu W, Ge X, You T, et al. Human CD59 inhibitor sensitizes rituximab-resistant lymphoma cells to complement-mediated cytolysis. Cancer Res. 2011; 71(6):2298-2307.
40. Suzuki M, Yamanoi A, Machino Y, et al. Effect of trastuzumab interchain disulfide bond cleavage on Fcgamma receptor binding and antibody-dependent tumour cell phagocytosis. J Biochem. 2016; 159(1):67-76.
41. Lazar G A, Dang W, Karki S, et al. Engineered antibody Fc variants with enhanced effector function. Proc Natl Acad Sci USA. 2006; 103(11):4005-4010.
42. Richards J O, Karki S, Lazar G A, Chen H, Dang W, Desjarlais J R. Optimization of antibody binding to FcgammaRIIa enhances macrophage phagocytosis of tumor cells. Mol Cancer Ther. 2008; 7(8):2517-2527.
43. Moore G L, Chen H, Karki S, Lazar G A. Engineered Fc variant antibodies with enhanced ability to recruit complement and mediate effector functions. MAbs. 2010; 2(2):181-189.
44. Diebolder C A, Beurskens F J, de Jong R N, et al. Complement is activated by IgG hexamers assembled at the cell surface. Science. 2014; 343(6176):1260-1263.
45. Sneller M C, Kopp W C, Engelke K J, et al. IL-15 administered by continuous infusion to rhesus macaques induces massive expansion of CD8+ T effector memory population in peripheral blood. Blood. 2011; 118(26): 6845-6848.
46. Imamura M, Shook D, Kamiya T, et al. Autonomous growth and increased cytotoxicity of natural killer cells expressing membrane-bound interleukin-15. Blood. 2014; 124(7):1081-1088.
47. Koh S, Shimasaki N, Bertoletti A. Redirecting T Cell Specificity Using T Cell Receptor Messenger RNA Electroporation. Methods Mol Biol. 2016; 1428:285-296.
48. de Jong R N, Beurskens F J, Verploegen S, et al. A Novel Platform for the Potentiation of Therapeutic Antibodies Based on Antigen-Dependent Formation of IgG Hexamers at the Cell Surface. PLoS Biol. 2016; 14(1):e1002344.

What is claimed is:

1. A T lymphocyte cell or natural killer cell that expresses a peptide, wherein the peptide comprises:

a) a single-chain variable fragment (scFv) domain that comprises:
   - i) an immunoglobulin variable light ($V_L$) domain;
   - ii) an immunoglobulin variable heavy ($V_H$) domain; and
   - iii) a linker domain joining the $V_L$ and $V_H$ domains, wherein the linker domain joining the $V_L$ and $V_H$ domains comprises SEQ ID NO: 5, wherein the scFv binds CD19 or CD20;

b) a hinge and constant heavy 2 ($C_H2$) and constant heavy 3 ($C_H3$) of IgG1 domain that is C-terminal to the scFv domain;

c) a CD8a signal peptide that is N-terminal to the scFv domain; and d) a linker domain that is C-terminal to the constant heavy 3 ($C_H3$) of IgG1 domain and joins an IL-15 domain, wherein the linker domain that is C-terminal to the $C_H3$ of IgG1 domain and joins the IL-15 domain comprises SEQ ID NO: 52.

2. The T lymphocyte cell or natural killer cell of claim 1, wherein the hinge and constant heavy 2 ($C_H2$) and constant heavy 3 ($C_H3$) of IgG1 domain is SEQ ID NO: 10.

3. The T lymphocyte cell or natural killer cell of claim 1, wherein the immunoglobulin variable light ($V_L$) domain is SED ID NO: 4 and the immunoglobulin variable heavy ($V_H$) domain is SED ID NO: 8.

* * * * *